(12) United States Patent
Johnson et al.

(10) Patent No.: US 10,987,466 B2
(45) Date of Patent: Apr. 27, 2021

(54) NEEDLE CONTROL AND DRUG MIXING SYSTEMS FOR A FLUID DELIVERY DEVICE

(71) Applicant: Valeritas, Inc., Bridgewater, NJ (US)

(72) Inventors: Matthew P. Johnson, Boylston, MA (US); Christopher C. Gregory, Newtown, PA (US)

(73) Assignee: ZEALAND PHARMA A/S, Soborg (DK)

(*) Notice: Subject to any disclaimer, the term of this patent is extended or adjusted under 35 U.S.C. 154(b) by 456 days.

(21) Appl. No.: 15/739,194

(22) PCT Filed: Jun. 30, 2016

(86) PCT No.: PCT/US2016/040281
§ 371 (c)(1),
(2) Date: Dec. 22, 2017

(87) PCT Pub. No.: WO2017/004315
PCT Pub. Date: Jan. 5, 2017

(65) Prior Publication Data
US 2018/0193557 A1 Jul. 12, 2018

Related U.S. Application Data

(60) Provisional application No. 62/188,464, filed on Jul. 2, 2015.

(51) Int. Cl.
*A61M 5/158* (2006.01)
*A61M 5/142* (2006.01)
(Continued)

(52) U.S. Cl.
CPC .......... *A61M 5/158* (2013.01); *A61M 5/1452* (2013.01); *A61M 5/14248* (2013.01);
(Continued)

(58) Field of Classification Search
CPC .............. A61M 5/158; A61M 5/14526; A61M 5/1452; A61M 5/14248;
(Continued)

(56) References Cited

U.S. PATENT DOCUMENTS 2,118,221 A    5/1938 Montouri
6,248,093 B1   6/2001 Moberg
(Continued)

FOREIGN PATENT DOCUMENTS

CN    101868273 A    10/2010
CN    102665799 A    9/2012
(Continued)

OTHER PUBLICATIONS

Office Action dated Dec. 20, 2018 for Japanese Patent Application No. 2017-564816, 5 pages.
(Continued)

*Primary Examiner* — Lauren P Farrar
(74) *Attorney, Agent, or Firm* — Morgan, Lewis & Bockius LLP

(57) ABSTRACT

A fluid delivery device comprises a housing having a base including a bottom surface; a locking assembly including a cartridge receiver configured to receive a cartridge, the cartridge having a fluid reservoir and a septum configured to be generally perpendicular to the bottom surface when the cartridge is engaged with the cartridge receiver; and a needle assembly having a needle, the needle having a delivery end, a fluid coupling end, and a central portion located between the delivery end and the fluid coupling end, the needle assembly configured to move in laterally relative to the base to a first position and vertically relative to the base to a second position. The locking assembly prevents the needle
(Continued)

assembly from moving to one or both of the first and second positions unless the cartridge is engaged with the cartridge receiver.

19 Claims, 12 Drawing Sheets

(51) Int. Cl.
  *A61M 5/145* (2006.01)
  *A61M 5/24* (2006.01)
  *A61M 5/32* (2006.01)
(52) U.S. Cl.
  CPC ......... *A61M 5/14526* (2013.01); *A61M 5/322* (2013.01); *A61M 2005/14252* (2013.01); *A61M 2005/14256* (2013.01); *A61M 2005/1581* (2013.01); *A61M 2005/247* (2013.01)
(58) Field of Classification Search
  CPC .. A61M 2005/14256; A61M 2005/247; A61M 2005/1581; A61M 5/322; A61M 2005/14252
  See application file for complete search history.

(56) References Cited

U.S. PATENT DOCUMENTS

| | | | |
|---|---|---|---|
| 7,455,663 B2 | 11/2008 | Bikovsky | |
| 8,740,847 B2 | 6/2014 | Levesque et al. | |
| 2002/0007671 A1 | 1/2002 | Lavi et al. | |
| 2004/0171991 A1* | 9/2004 | Cherif-Cheikh | A61M 5/3257 604/198 |
| 2005/0171476 A1 | 8/2005 | Judson et al. | |
| 2009/0093792 A1 | 4/2009 | Gross et al. | |
| 2011/0060310 A1 | 3/2011 | Prestrelski et al. | |
| 2013/0046239 A1 | 2/2013 | Gonnelli et al. | |
| 2016/0082182 A1* | 3/2016 | Gregory | A61M 5/14248 604/150 |

FOREIGN PATENT DOCUMENTS

| | | |
|---|---|---|
| JP | H5-31191 A | 2/1998 |
| JP | 2010-540156 A | 12/2010 |
| WO | 2012032411 A2 | 3/2012 |
| WO | 2014/194183 A2 | 12/2014 |
| WO | WO-2014194183 A2 * 12/2014 | ........ A61M 5/14526 |

OTHER PUBLICATIONS

Extended European Search Report dated Jan. 7, 2019 for European Patent Application No. 16818750.8, 11 pages.
International Search Report, dated Nov. 4, 2016, for International Patent Application No. PCT/US2016/040281.
Written Opinion of the International Searching Authority, dated Nov. 4, 2016, for International Application No. PCT/US2016/040281.
First Office Action for Chinese Patent Application No. 201680048925.0, 27 pages.

* cited by examiner

NEEDLE CONTROL AND DRUG MIXING SYSTEMS FOR A FLUID DELIVERY DEVICE

CROSS-REFERENCE TO RELATED APPLICATIONS

This application is a U.S. National Stage of International Patent Application No. PCT/US2016/040281 filed Jun. 30, 2016, which claims the benefit of U.S. Provisional Patent Application No. 62/188,464 filed Jul. 2, 2015 and entitled "Needle Control and Drug Mixing Systems for a Fluid Delivery Device," each of which is incorporated by reference herein in its entirety.

BACKGROUND OF THE INVENTION

The present invention generally relates to a fluid delivery device and, in some embodiments, to a needle control system for a fluid delivery device and a drug mixing system for a fluid delivery device.

BRIEF SUMMARY OF THE INVENTION

In one embodiment there is a fluid delivery device comprising: a housing having a base including a bottom surface; a locking assembly including a cartridge receiver configured to receive a cartridge, the cartridge having a fluid reservoir and a septum configured to be generally perpendicular to the bottom surface when the cartridge is engaged with the cartridge receiver; and a needle assembly having a needle, the needle having a delivery end, a fluid coupling end, and a central portion located between the delivery end and the fluid coupling end, the needle assembly configured to move laterally relative to the base to a first position and vertically relative to the base to a second position. In some embodiments the locking assembly prevents the needle assembly from moving to one or both of the first and second positions unless the cartridge is engaged with the cartridge receiver.

In some embodiments the locking assembly prevents the needle assembly from moving to the first position unless the cartridge is engaged with the cartridge receiver. In some embodiments the locking assembly prevents the needle assembly from moving to the second position unless the cartridge is engaged with the cartridge receiver.

In some embodiments the needle assembly is configured to be moveable to one of the first and second positions only after being moved to the other of the first and second positions. In some embodiments the needle assembly is configured to be moveable to the first position only after being moved to the second position. In some embodiments the needle assembly is configured to be moveable to the second position only after being moved to the first position.

In some embodiments the fluid coupling end is fluidly coupled with the fluid reservoir in the first position. In one embodiment the delivery end is deployed into a patient's skin in the second position.

In one embodiment there is a fluid delivery device comprising: a housing having a base including a bottom surface and a cartridge receiver configured to receive a cartridge, the cartridge having a fluid reservoir and a septum configured to be generally perpendicular to the bottom surface when the cartridge is engaged with the cartridge receiver; and a needle assembly having a needle, the needle having a delivery end, a fluid coupling end, and a central portion located between the delivery end and the fluid coupling end, the fluid coupling end being fluidly disengaged from the fluid reservoir in an initial position, the fluid delivery device having a primed position in which the fluid coupling end being fluidly coupled with the fluid reservoir. In some embodiments the needle assembly is configured to translate laterally relative to the base from the initial position to the primed position. In some embodiments the cartridge receiver has a locked position in which the needle assembly is retained in the initial position and an unlocked position in which the needle assembly is able to translate from the initial position to the primed position. In some embodiments the cartridge receiver is configured to be in the locked position when the cartridge receiver is not engaged with the cartridge and configured to be in the unlocked position when the cartridge receiver is engaged with the cartridge.

In some embodiments the needle assembly has a stop, the cartridge receiver abutting the stop in the locked position to retain the needle assembly in the initial position.

In some embodiments the fluid delivery device has an opening for receiving the cartridge and the cartridge receiver is configured to protrude into the opening at a first angle relative to the base when the cartridge is not engaged with the cartridge receiver.

In some embodiments the cartridge receiver is configured to flex to a second angle relative to the base in response to engagement with the cartridge, wherein the first angle is greater than the second angle.

In some embodiments an axis extending between the needle delivery end and the central portion is generally orthogonal to an axis extending between the needle fluid coupling end and the central portion. In some embodiments the needle central portion defines a coil.

In some embodiments a fluid delivery device further comprises an actuator and a hydraulic chamber. In some embodiments the actuator is configured to deliver a force to the cartridge through a fluid contained in the hydraulic chamber.

In one embodiment there is a fluid delivery device comprising: a housing having a base configured to receive a cartridge, the base having a bottom surface configured to be coupled to a skin surface in an engaged position and a base lock, the cartridge having a fluid reservoir and a septum configured to be generally perpendicular to the bottom surface when the cartridge is inserted in the housing; and a needle assembly having a needle and a needle lock, the needle having a delivery end, a fluid coupling end, and a central portion located between the delivery end and the fluid coupling end. In some embodiments the fluid coupling end is fluidly disengaged from the fluid reservoir in an initial position, the fluid coupling end being fluidly coupled with the fluid reservoir in both a primed position and a deployed position, and the delivery end extending past the bottom surface of the base in the deployed position. In some embodiments the needle assembly is configured to translate laterally relative to the base from the initial position to the primed position and translate vertically relative to the base from the primed position to the deployed position. In some embodiments the base lock is configured to mate with the needle lock to prevent the needle assembly from translating vertically when the needle assembly is in the initial position and wherein the base lock is configured to be unmated from the needle lock to allow the needle assembly to translate vertically when the needle assembly is in the primed position.

In some embodiments an axis extending between the needle delivery end and the central portion is generally orthogonal to an axis extending between the needle fluid coupling end and the central portion. In some embodiments the needle central portion defines a coil. In some embodiments the needle central portion coil has a length that is configured to be compressed as the needle assembly translates from the primed position to the deployed position.

In some embodiments a needle assembly further comprising: a needle assembly core and a needle assembly head, the distal end of the needle extending along the axial direction through the needle core and the needle assembly head defining a channel sized and configured to receive the needle assembly core. In some embodiments the needle assembly core has a latch and the needle assembly head having a protrusion and in some embodiments the latch is configured to releasably engage with the protrusion to lock the needle assembly in the deployed position.

In some embodiments a needle assembly further comprises: a needle assembly core and a needle assembly head, the distal end of the needle extending along the axial direction through the needle core and the needle assembly head defining a channel sized and configured to receive the needle assembly core. In some embodiments the needle assembly core has a protrusion and the needle assembly head has a latch. In some embodiments the latch is configured to releasably engage with the protrusion to lock the needle assembly in the deployed position.

In some embodiments a fluid delivery device further comprises a needle release assembly having a needle release button configured to disengage the latch from the protrusion when actuated.

In some embodiments the needle central portion coil is sized and configured to not fit within the channel and wherein the needle central portion coil is biased against the needle assembly head in the deployed position. In some embodiments the needle central portion coil is sized and configured to surround a spring that is biased against the needle assembly head in the deployed position. In some embodiments the central portion coil is configured to retract the needle assembly from the deployed position to the retracted position when the needle release button is actuated.

In some embodiments the base further has a retention hook and the needle release assembly further has a torsion spring biased against the needle release button, the torsion spring having a first leg and a second leg, the first leg engaged with the needle release button and the second leg configured to releasably engage with the retention hook in the initial, primed, and deployed positions, and configured to extend into the needle assembly channel, substantially perpendicular to the axis of the channel, in the retracted position. In some embodiments the torsion spring has a cross section with a first axis larger than a second axis, wherein the second axis is oriented orthogonal to the first axis. In some embodiments the torsion spring has a rectangular cross section, while in other embodiments the torsion spring has a circular cross section.

In some embodiments a fluid delivery device further comprises: an actuator and a hydraulic chamber. In some embodiments the actuator is configured to deliver a force to the cartridge through a fluid contained in the hydraulic chamber.

In some embodiments a fluid delivery device further comprises a cartridge receiver, the cartridge receiver having a locked position in which the needle assembly is retained in the initial position and an unlocked position in which the needle assembly is able to translate from the initial position to the primed position; and the cartridge receiver configured to be in the locked position when the cartridge receiver is not engaged with the cartridge and configured to be in the unlocked position when the cartridge receiver is engaged with the cartridge.

In one embodiments there is a fluid delivery device comprising: a housing; a cartridge configured to be inserted into the fluid delivery device housing, the cartridge having a septum having a pierceable portion, a first slidable piston, a first reservoir between the first slidable piston and the septum, a second slidable piston, a second reservoir formed between the first slidable piston and the second slidable piston, and a piston bypass fluidly coupling the first reservoir and the second reservoir when the first slidable piston is positioned in axial alignment with the piston bypass; a needle assembly having a needle, the needle having a delivery end, a fluid coupling end, and a central portion located between the delivery end and the fluid coupling end, the fluid coupling end being fluidly disengaged from the fluid reservoir in an initial position, the fluid coupling end being fluidly coupled with the fluid reservoir in a primed position, the needle assembly being configured to be moved from the initial position to the primed position; and an actuator configured to push the second slidable piston into physical contact with the first slidable piston.

In some embodiments the first reservoir is prefilled with a first material and the second reservoir is prefilled with a second material. In some embodiments one of the first and second materials is a diluent and the other of the first and second materials is a medicament. In some embodiments the first material is a medicament and the second material is a diluent. In some embodiments the first material is a first medicament and the second material is a second medicament.

In some embodiments the actuator comprises a bolus piston that is configured to push a hydraulic fluid toward the second slidable piston. In some embodiments the actuator includes a stem configured to push the bolus piston toward the hydraulic fluid. In some embodiments the stem is directly coupled to the second slidable piston. In some embodiments the stem is coupled to a hydraulic fluid that is coupled to the second slidable piston. In some embodiments the stem is a pawl.

In some embodiments the actuator comprises a button that is in physical communication with the stem and is configured to be pushed by a user toward the stem.

In one embodiment there is a method of mixing a first material and a second material in a fluid delivery device, the fluid delivery device including hydraulic drive fluid, the method comprising: inserting a cartridge into the fluid delivery device, the cartridge having a septum, a first slidable piston, a first reservoir between the first slidable piston and the septum containing a first material, a second slidable piston, a second reservoir formed between the first slidable piston and the second slidable piston containing a second material, and a piston bypass; and displacing the hydraulic drive fluid, wherein the hydraulic fluid is in mechanical communication with the second slidable piston, to displace the second slidable piston towards the first slidable piston, wherein the second material is urged through the piston bypass into the first reservoir as the second slidable piston is brought into contact with the first slidable piston. In some embodiments the displacing is stepwise. In some embodiments displacing is performed by pressing a button.

In one embodiment there is a fluid delivery device that includes a housing and a needle assembly. The housing may have a base including a bottom surface and a cartridge receiver configured to receive a cartridge, the cartridge having a fluid reservoir and a septum configured to be generally perpendicular to the bottom surface when the cartridge is engaged with the cartridge receiver. The needle assembly may have a needle, the needle having a delivery end, a fluid coupling end, and a central portion located between the delivery end and the fluid coupling end, the fluid coupling end being fluidly disengaged from the fluid reservoir in an initial position, the fluid coupling end being fluidly coupled with the fluid reservoir in a primed position, the needle assembly being configured to translate laterally relative to the base from the initial position to the primed position. In some embodiments the cartridge receiver has a locked position in which the needle assembly is retained in the initial position and an unlocked position in which the needle assembly is able to translate from the initial position to the primed position. The cartridge receiver may be configured to be in the locked position when the cartridge receiver is not engaged with the cartridge and configured to be in the unlocked position when the cartridge receiver is engaged with the cartridge.

In some embodiments of a fluid delivery device that includes a housing and a needle assembly, the needle assembly has a stop and the cartridge receiver abuts the stop in the locked position to retain the needle assembly in the initial position. The fluid delivery device may have an opening for receiving the cartridge and the cartridge receiver is configured to protrude into the opening at a first angle relative to the base when the cartridge is not engaged with the cartridge receiver. The cartridge receiver may be configured to flex to a second angle relative to the base in response to engagement with the cartridge, wherein the first angle is greater than the second angle. In some embodiments the needle assembly is configured to translate vertically relative to the base to a deployed position. In some embodiments, the needle assembly is configured to be moveable to the deployed position only after being moved to the primed position, wherein the needle delivery end extends past the bottom surface of the base in the deployed position.

In some embodiments of a fluid delivery device an axis extending between the needle delivery end and the needle central portion is generally orthogonal to an axis extending between the needle fluid coupling end and the needle central portion. In some embodiments the needle central portion defines a coil. The needle central portion coil may have a length that is configured to be deformed as the needle assembly translates from the primed position to the deployed position.

In some embodiments of a fluid delivery device that includes a housing and a needle assembly further includes an actuator and a hydraulic chamber. The actuator may be configured to deliver a force to the cartridge through a fluid contained in the hydraulic chamber.

In some embodiments of a fluid delivery device that includes a housing and a needle assembly, the needle assembly further includes a needle assembly core and a needle assembly head, the distal end of the needle extending along the axial direction through the needle core and the needle assembly head defining a channel sized and configured to receive the needle assembly core, the needle assembly core having one of a latch and a protrusion, the needle assembly head having the other of a latch and a protrusion. The latch may be configured to releasably engage with the protrusion to lock the needle assembly in the deployed position.

In some embodiments a fluid delivery device may further comprise a needle release assembly having a needle release button configured to disengage the latch from the protrusion when actuated. In some embodiments the needle central portion coil is configured to retract the needle assembly from the deployed position to a retracted position when the needle release button is actuated, wherein the needle delivery end does not extend past the bottom surface of the base in the retracted position. In some embodiments, the base further has a retention hook and the needle release assembly further has a torsion spring biased against the needle release button, the torsion spring having a first leg and a second leg, the first leg engaged with the needle release button and the second leg configured to releasably engage with the retention hook in the initial, primed, and deployed positions, and configured to extend into the needle assembly head channel, substantially perpendicular to the axis of the channel, in the retracted position. The tension spring may have a rectangular cross-section, or may have a circular cross-section.

In one embodiment a cartridge is configured to be inserted into a fluid delivery device comprising a housing and a needle assembly. The cartridge may include a septum having a pierceable portion, a first slidable piston, a first reservoir between the first slidable piston and the septum, a second slidable piston, a second reservoir formed between the first slidable piston and the second slidable piston, and a piston bypass fluidly coupling the first reservoir and the second reservoir when the first slidable piston is positioned in axial alignment with the piston bypass. The second slidable piston may be configured to be pushed into physical contact with the first slidable piston by the actuator. In some embodiments the first reservoir is prefilled with a first material and the second reservoir is prefilled with a second material. In some embodiments one of the first and second materials is a diluent and the other of the first and second materials is a medicament.

In one embodiment a method of mixing a first material and a second material in a fluid delivery device, the fluid delivery device including hydraulic drive fluid, includes inserting a cartridge into the fluid delivery device, the cartridge having a septum, a first slidable piston, a first reservoir between the first slidable piston and the septum containing a first material, a second slidable piston, a second reservoir formed between the first slidable piston and the second slidable piston containing a second material, and a piston bypass; and displacing the hydraulic drive fluid, wherein the hydraulic fluid is in mechanical communication with the second slidable piston, to displace the second slidable piston towards the first slidable piston. The second material may be urged through the piston bypass into the first reservoir as the second slidable piston is brought into contact with the first slidable piston. In some embodiments the displacing is stepwise. In some embodiments the displacing is performed by pressing a button.

BRIEF DESCRIPTION OF THE SEVERAL VIEWS OF THE DRAWINGS

The following detailed description of embodiments of the needle control and drug mixing systems for a fluid delivery device will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

Figure 4:
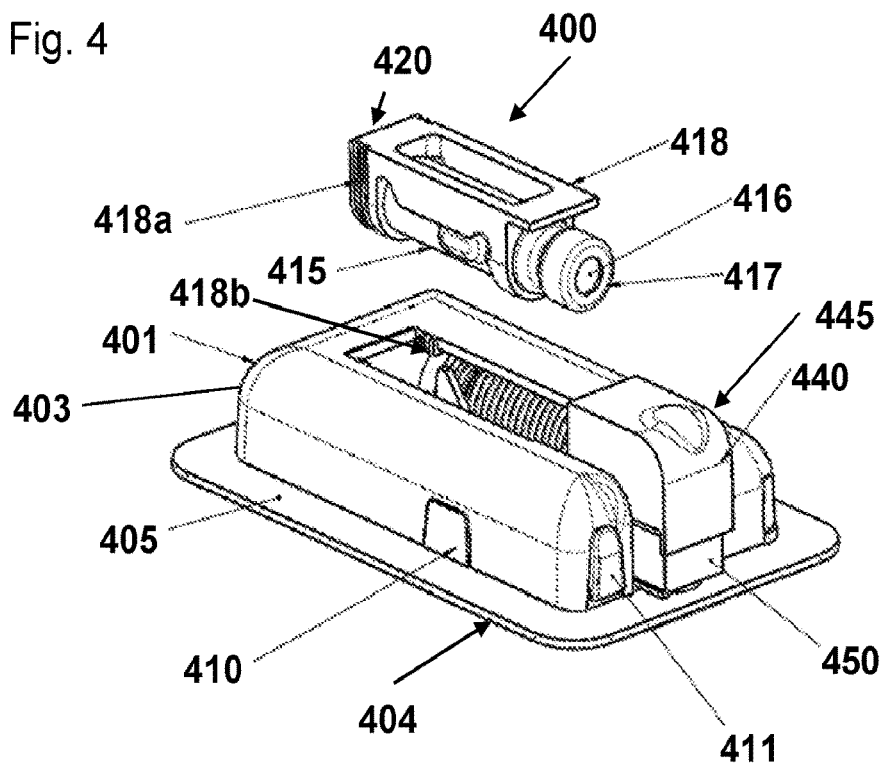
FIG. 4 is a trimetric view of a cartridge and base of a fluid delivery device in accordance with an exemplary alternative embodiment of the present invention.
Figure 5:
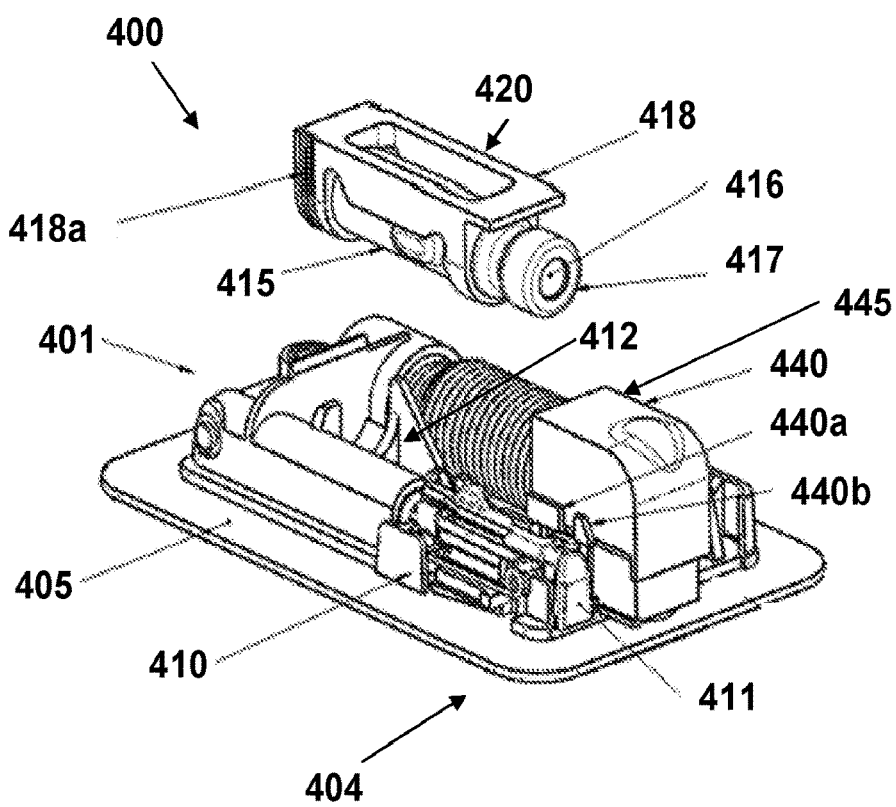
FIG. 5 is a trimetric view of the cartridge and base of the fluid delivery device shown in FIG. 4, with the cover removed for clarity.
Figure 6:
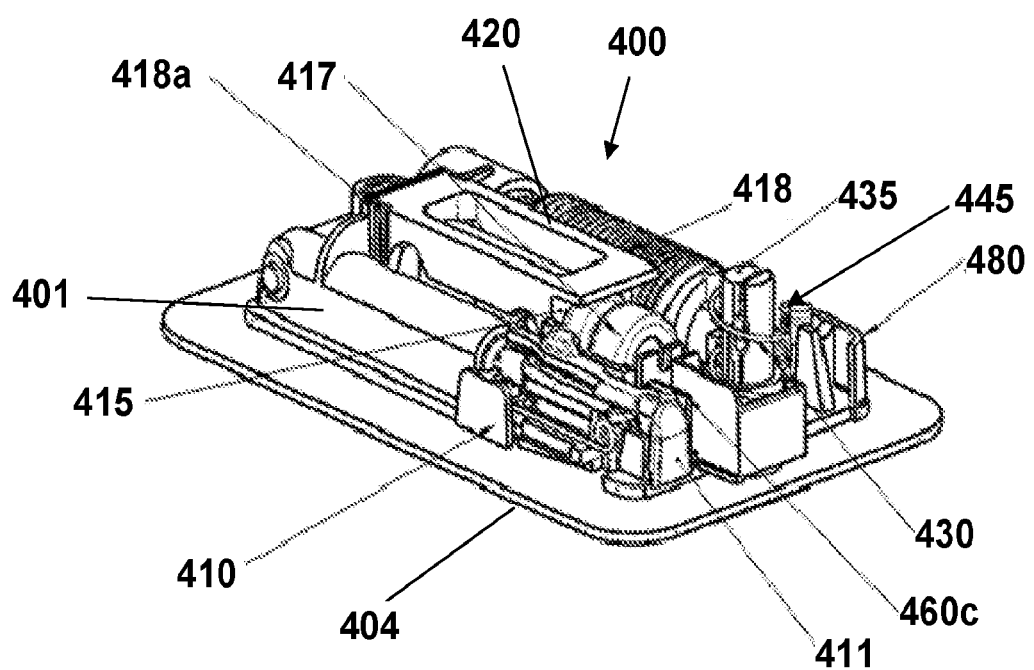
FIG. 6 is a trimetric view of the cartridge inserted in the base of the fluid delivery device shown in FIG. 4, with the cover and cap removed for clarity.

Referring to the drawings in detail, wherein like reference numerals indicate like elements throughout, there is shown in FIGS. 4-6 a fluid delivery device, generally designated 400, in accordance with an exemplary embodiment of the present invention. A fluid device delivery device may include one or more features described herein, such as needle assembly 445 shown in detail in FIGS. 7A-7E, and cartridge assembly 420, shown in detail in FIGS. 16B-17.

Embodiments of the needle control and drug mixing systems for a fluid delivery device described herein may be used with various fluid delivery devices, such as prior art fluid delivery device 110 (see FIGS. 1-3B), disclosed in U.S. Patent Application Publication No. 2013/0046239, U.S. Pat. Nos. 8,740,847, and 7,481,792, each of which is hereby incorporated by reference in its entirety.

Figure 1:
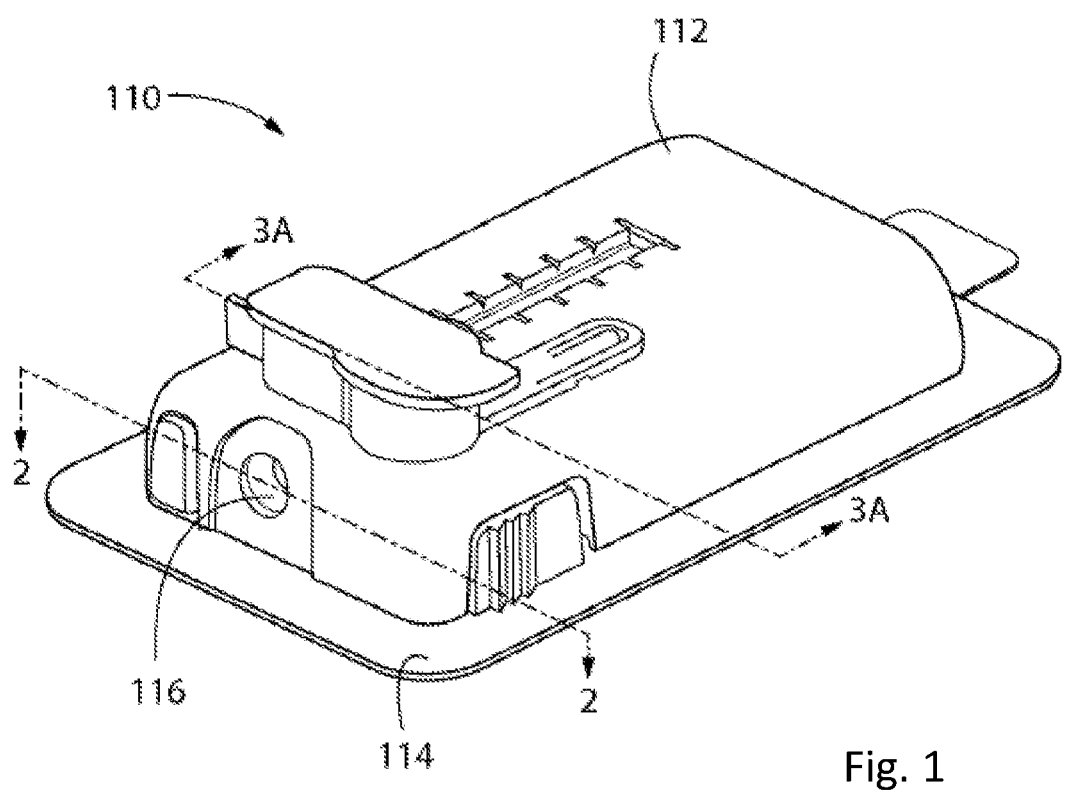
FIG. 1 is a trimetric view of a prior art fluid delivery device.
Figure 2:
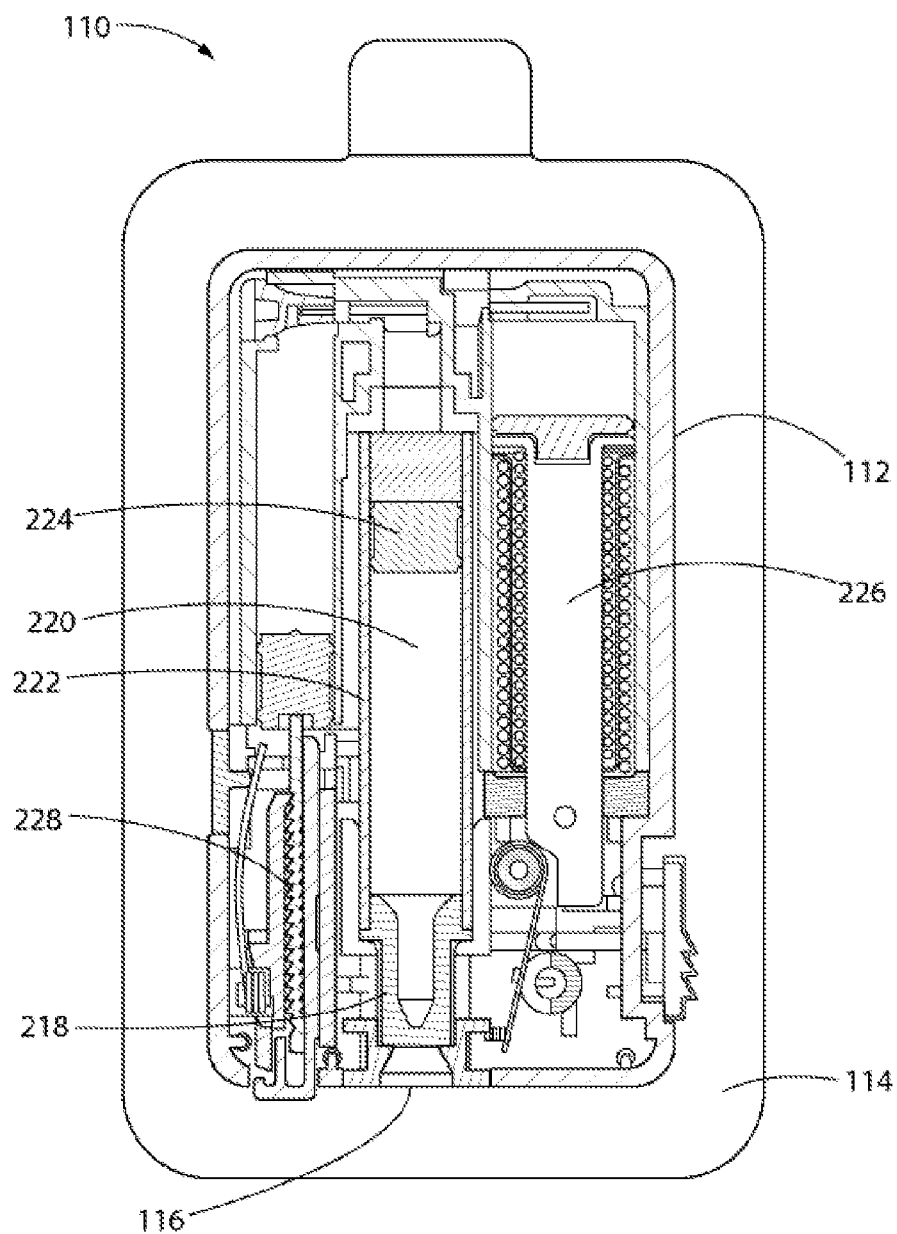
FIG. 2 is a top cross sectional view of the fluid delivery device shown in FIG. 1 taken along a plane location and direction indicated by line 2-2.

Referring to FIGS. 1-3, fluid delivery device 110 is shown. In one embodiment, fluid delivery device 110 is a discrete ambulatory insulin delivery pump. Fluid delivery device 110 may be single use, disposable and incapable of reuse. Fluid delivery device 110 may provide therapeutic capability in a small, single use, disposable package and can be produced using high volume manufacturing fabrication (e.g., injection molding) and assembly processes, allowing for low cost-of goods. Devices of the invention can be used for a broad range of applications, including, but not limited to, clinical applications (administration of medicaments, etc.) and biomedical research (e.g., microinjection into cells, nuclear or organelle transplantation, isolation of single cells or hybridomas, etc.).

In one embodiment, fluid delivery device 110 is a device for dispensing, delivering, or administering a fluid or agent to the user or patient. The fluid may be a low viscosity gel agent and or a therapeutic agent. In one embodiment, the fluid includes an analgesic agent. In one embodiment, the fluid includes insulin. In one embodiment, the fluid includes a U100 insulin. In another embodiment the fluid includes a U200 insulin. In another embodiment the fluid includes a U300 insulin. In another embodiment, the fluid includes a U500 insulin. In another embodiment the fluid includes any insulin concentration. In another embodiment the fluid includes Glucagon-like peptide-1 (GLP-1). In other embodiments, the fluid may include, but is not limited to including, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using fluid delivery device 110. As used herein "patients" or "user" can be human or non-human animals; the use of fluid delivery device 110 is not confined solely to human medicine, but can be equally applied to veterinarian medicine.

Fluid delivery device 110 may dispense the fluid over a sustained period of time (i.e., basal delivery). In one embodiment, the fluid delivery rate is continuously or near continuously delivered to the user over the sustained period of time. Fluid delivery device 110 may also be capable of dispensing a supplementary amount of fluid, in addition to the basal amount, on demand, under patient control (i.e., bolus delivery). In one embodiment, the bolus amount delivered in a single, selectable administration is pre-determined. In preferred embodiments, fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Referring to FIG. 1, for example, the fluid delivery device 110 shown includes a housing 112 and an adhesive bottom surface 114 such as a foam pad. Fluid delivery device 110 includes a fill port 116 to access a pierceable septum 218. In another embodiment, fluid delivery device 110 is filled through the insertion of one or more pre-filled cartridges. Referring to FIG. 2, fluid delivery device 110 includes a cartridge 222 having a fluid reservoir 220 containing a fluid (e.g. a medicament). The fluid delivery device 110 may include one or more actuators 226 (such as a basal actuator) and/or 228 (such as a bolus actuator) that act on piston 224 within cartridge 222.

Figure 3A:
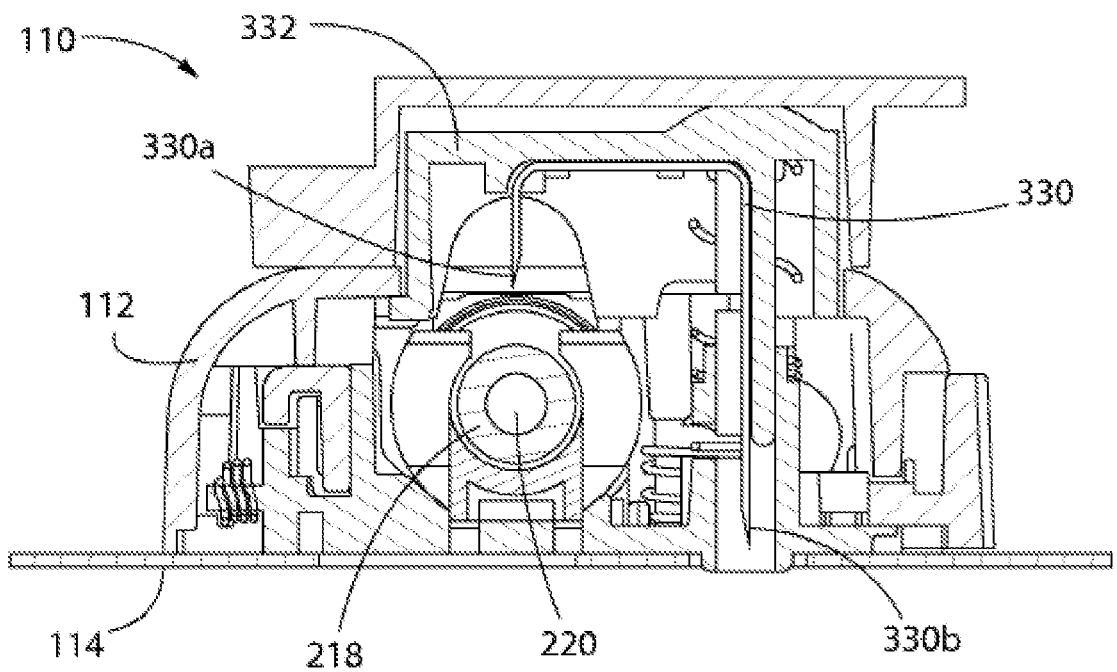
FIG. 3A is a front cross sectional view of the fluid delivery device shown in FIG. 1 taken along a plane location and direction indicated by line 3A-3A.
Figure 3B:
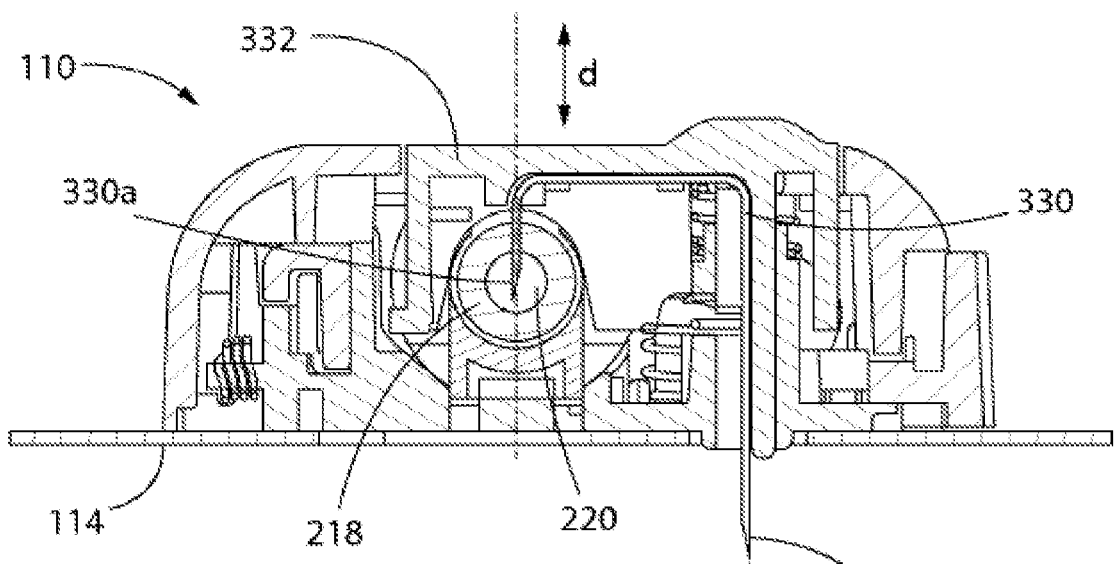
FIG. 3B is a front cross sectional view of the fluid delivery device of FIG. 3A shown in the deployed position.

Referring to FIGS. 3A and 3B, a needle 330 may be deployed to fluidly couple fluid reservoir 220 and the patient. Needle 330 may be coupled to a button 332 and the needle 330 may be bent such that a translation of button 332 toward the patient causes a fluid coupling end 330a to be fluidly coupled to fluid reservoir 220 and a delivery end 330b to extend from bottom surface 114.

Referring now to FIGS. 4-6, an exemplary fluid delivery device 400 is shown. In one embodiment, fluid delivery device 400 is a discrete ambulatory insulin delivery pump. Fluid delivery device 400 may be single use, disposable and incapable of reuse. Fluid delivery device 400 may provide therapeutic capability in a small, single use, disposable package and can be produced using high volume manufacturing fabrication (e.g., injection molding) and assembly processes, allowing for low cost-of goods. Devices of the invention can be used for a broad range of applications, including, but not limited to, clinical applications (administration of medicaments, etc.) and biomedical research (e.g., microinjection into cells, nuclear or organelle transplantation, isolation of single cells or hybridomas, etc.).

In one embodiment, fluid delivery device 400 is a device for dispensing, delivering, or administering a fluid or agent to the user or patient. The fluid may be a low viscosity gel agent and or a therapeutic agent. In one embodiment, the fluid includes an analgesic agent. In one embodiment, the fluid includes insulin. In one embodiment, the fluid includes a U100 insulin. In another embodiment the fluid includes a U200 insulin. In another embodiment the fluid includes a U300 insulin. In another embodiment, the fluid includes a U500 insulin. In another embodiment the fluid includes any insulin concentration. In another embodiment the fluid includes Glucagon-like peptide-1 (GLP-1). In other embodiments, the fluid may include, but is not limited to including, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using fluid delivery device 400. As used herein "patients" or "user" can be human or non-human animals; the use of fluid delivery device 400 is not confined solely to human medicine, but can be equally applied to veterinarian medicine.

Fluid delivery device 400 may dispense the fluid over a sustained period of time (i.e., basal delivery). In one embodiment, the fluid delivery rate is continuously or near continuously delivered to the user over the sustained period of time. Fluid delivery device 400 may also be capable of dispensing a supplementary amount of fluid, in addition to the basal amount, on demand, under patient control (i.e., bolus delivery). In one embodiment, the bolus amount delivered in a single, selectable administration is pre-determined. With reference to FIGS. 16B-18, in preferred embodiments, fluid delivery device 400 is hydraulically actuated by one or more actuators 426 (such as a basal actuator) and/or 428 (such as a bolus actuator) that act on piston 427 within cartridge 420, and the fluid delivery device 400 comprises one or more reservoirs or chambers containing hydraulic fluid (or, depending on the reservoir, another fluid, e.g. a diluent or medicament) of a suitable viscosity for transferring power from one or more actuators to the fluid and controlling the delivery rate as discussed further below.

Referring to FIGS. 4-6, in some embodiments, the fluid delivery device 400 includes a bottom surface 404 configured to be coupled to a skin surface in an engaged position. Alternatively, bottom surface 404 may be configured to be coupled to an adhesive pad, which in turn may be coupled to a skin surface in an engaged position. In one embodiment, the patient inserts a cartridge 420 into the fluid delivery device 400 prior to use. In one embodiment, a cartridge 420 having a fluid reservoir 415 is coupled to the fluid delivery device 400 and has a septum 416. In one embodiment, the septum 416 seals one end of the fluid reservoir 415 and a second piston 425 (see FIG. 16B) seals the other end. The septum 416 of the cartridge 420 may have a pierceable portion, the portion of the septum 416 pierced by the needle 430 during use. In one embodiment, the cartridge 420 is comprised of glass, or has an inner glass coating, though other materials for the cartridge 420 such as plastic may be used. In one embodiment a cartridge 420 can have a silicone coating on the glass or plastic.

Referring to FIGS. 7A-7E, in some embodiments, a needle assembly 445 having a needle 430 may be used to fluidly couple the fluid reservoir 415 through the septum 416 with tissue under the skin surface with the desired motion by the user or be configured to automatically deploy upon use of the fluid delivery device 400. The needle 430 may have a delivery end 430c, a fluid coupling end 430a, and a needle center portion 430b located between the delivery end 430c and the fluid coupling end 430a. Initially, the fluid coupling end 430a may be fluidly disengaged from the fluid reservoir 415, (e.g., an initial, storage, or pre-fluid delivery position). After the fluid delivery device 400 is adhered to the skin surface and the needle 430 is in the engaged position, the needle delivery end 430c may be extended past the bottom surface 404 and/or the adhesive pad 405 of the fluid delivery device 400 and the needle fluid coupling end 430a may be extended through the pierceable portion of the septum 416 either simultaneously, at offset times or separately such that the fluid reservoir 415 is fluidly coupled with the patient during use (e.g., a deployed, in-use, or fluid delivery position). In some embodiments, the needle fluid coupling end 430a may be extended through the pierceable portion of the septum 416 before the needle delivery end 430c is extended past the bottom surface 404 and/or adhesive pad 405 of the fluid delivery device 400, (e.g. a primed position). After a fluid has been delivered to a patient through the needle fluid coupling end 430a and the needle delivery end 430c, the needle delivery end 430c may be withdrawn from the skin surface, (e.g. to a retracted position).

Figure 9:
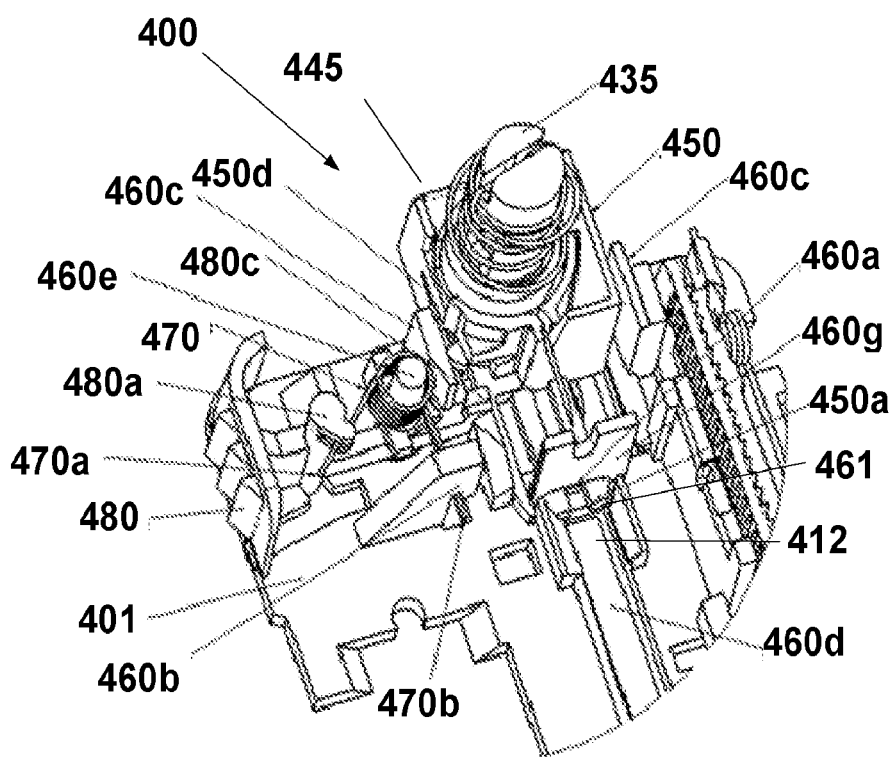
FIG. 9 is a trimetric detail view of the assembled embodiment shown in FIG. 4 ready for the insertion of the medicament cartridge assembly with the cover, needle assembly cap, spring drive removed for clarity.

Referring to FIG. 9, in an embodiment a fluid delivery device 400 includes a base 401 including a bottom surface 404; a locking assembly 461 including a cartridge receiver (also referred to herein as a flexing feature or receiving arm) 460d configured to receive a cartridge 420, the cartridge 420 having a fluid reservoir 415 and a septum 416 configured to be generally perpendicular to the bottom surface 404 when the cartridge 420 is engaged with the base 401; and a needle assembly 445 having a needle 430, the needle 430 having a needle delivery end 430c, a needle fluid coupling end 430a, and a needle center portion 430b located between the needle delivery end 430c and the needle fluid coupling end 430a, the needle assembly 445 configured to move laterally relative to the base 401 to a first position and vertically relative to the base 401 to a second position. In an embodiment the locking assembly 461 prevents the needle assembly 445 from moving to one or both of the first and second positions unless the cartridge 420 is engaged with the cartridge receiver 460d. In an embodiment the cartridge receiver 460d of the locking assembly 461 prevents the needle assembly 445 from moving to the first position unless the cartridge 420 is engaged with the cartridge receiver 460d. In another embodiment the cartridge receiver 460d of the locking assembly 461 prevents the needle assembly 445 from moving to the second position unless the cartridge 420 is engaged with the cartridge receiver 460d. In another embodiment the needle assembly 445 may be moved simultaneously into the first and second positions once the cartridge 420 is engaged with the cartridge receiver 460d.

In an embodiment the needle assembly 445 is configured to be moveable to one of the first and second positions only after being moved to the other of the first and second positions. For example, the needle assembly 445 may be configured to be moveable to the first position only after being moved to the second position, or the needle assembly 445 may be configured to be moveable to the second position only after being moved to the first position. The needle fluid coupling end 430a may be fluidly coupled with the fluid reservoir 415 in the first position. The needle delivery end 430c may be deployed into a patient's tissue in the second position.

A fluid delivery device 400 may include a base 401 configured to receive a fluid cartridge 420. The base 401 may have a bottom surface 404 and a cartridge receiver 460d, the cartridge receiver 460d being configured to engage with a fluid cartridge 420. In some embodiments a fluid delivery device 400 may further include a needle assembly 445. The needle assembly 445 may include a needle 430 for communicating fluid from the fluid cartridge 420 to the body of a patient. The needle 430 may have a delivery end 430c, a fluid coupling end 430a and a needle center portion 430b located between the delivery end 430c and the fluid coupling end 430a. The fluid cartridge 420 may have a fluid reservoir 415 and a septum 416. In an embodiment the septum 416 is configured to be pierced by the needle fluid coupling end 430a. In an embodiment the septum 416 is configured to be generally perpendicular to the bottom surface 404 when the cartridge 420 is engaged with the cartridge receiver 460d. In another embodiment the septum 416 is configured to be generally parallel to the bottom surface 404 when the cartridge is engaged with the cartridge receiver 460d. In another embodiment the septum 416 is configured to be oriented at an angle from the bottom surface 404 when the cartridge 420 is engaged with the cartridge receiver 460d.

The needle assembly 445 of a fluid delivery device 440 may be configured to move relative to the base 401 of the fluid delivery device 400 in order to couple the needle fluid coupling end 430a to the fluid cartridge 420 and to inject the needle delivery end 430c into the patient. The needle fluid coupling end 430a may be fluidly disengaged from the fluid reservoir 415 in an initial (e.g. storage) position. The fluid coupling end 430a may be fluidly coupled with the fluid reservoir 415 in a primed position. The fluid coupling end 430a may be fluidly coupled with the fluid reservoir 415 and the delivery end 430c may extend past the bottom surface 404 and/or the adhesive pad 405 of the base 401 in a deployed position. Preferably, the delivery end 430c may extend past the bottom surface 404 of the base 401 and into the skin of a patient in a deployed position. The needle delivery end 430c may be retracted above the bottom surface 404 of the base 401 in a retracted position. Preferably, the needle delivery end 430a may be raised to the retracted position after the deployment.

In an embodiment the needle assembly 445 is configured to translate relative to the base 401 from the initial position to the primed position. In one embodiment the needle 430 is configured to translate laterally relative to the base 401 from the initial position to the primed position. In another embodiment the needle 430 is configured to translate vertically from the initial position to the primed position. In yet another embodiment the needle 430 is configured to rotate from the initial position to the primed position. In an embodiment the needle assembly 445 is configured to translate relative to the base 401 from the primed position to the deployed position. In another embodiment the needle 430 is configured to translate vertically from the primed position to the deployed position. In yet another embodiment the needle 430 is configured to rotate from the primed position to the deployed position. In a preferred embodiment the needle assembly 445 is configured to translate laterally relative to the base 401 from the initial position to the primed position and translate vertically relative to the base 401 from the primed position to the deployed position.

Referring to FIGS. 4-14, in an embodiment, the fluid delivery device 400 includes a base 401. In such embodiment an insertable cartridge assembly 420 may be provided separately. In another embodiment fluid delivery device 400 includes a base 401 and an insertable cartridge carrier 418 for providing outer support to a cartridge. In still another embodiment, fluid delivery device 400 includes a base 401 and an insertable cartridge assembly 420. The insertable cartridge assembly 420 may include a fluid reservoir 415 containing a material (e.g. a fluid or a medicament), sealed at one end with a pierceable element 416, such as a septum held in place by a crimp cover 417, and sealed at the other end by an internal movable piston (not shown), all held by an outer support part (e.g. cartridge carrier) 418.

In an embodiment as shown in FIG. 4, the base 401 has a housing 403. Referring to FIGS. 4 and 5, an adhesive pad 405 may be attached to the base 401 for securing the device 400 to the user. The base 401 may include a channel or opening 412 for receiving a fluid assembly cartridge 420. The channel or opening 412 in the base 401 for receiving the fluid cartridge assembly 420 may be bordered by a hydraulic drive interface at one end and a needle assembly 445 at the other end. In one embodiment, the fluid delivery device 400 also has a bolus delivery button 411 for delivering one or more bolus doses. The fluid delivery device 400 may also have a bolus release button 410 for unlocking the bolus delivery button 411.

The cartridge assembly 420 may be inserted in the channel or opening 412 in the base 401, as shown in FIG. 6. In a preferred embodiment the cartridge 420 is inserted into the fluid delivery device 400 with the pierceable septum 416 facing the needle assembly 445. Cartridge assembly 420 may comprise grooves 418a, which may mate with corresponding ribs 418b of housing 403. Grooves 418a helps to ensure a proper cartridge assembly 420 is inserted, ensure that cartridge assembly 420 is inserted correctly, and/or that cartridge assembly 420 maintains a proper seal with the base 401.

In an embodiment, a needle assembly 445 includes a needle assembly head 450 and needle assembly cap 440. The needle assembly 445 may control the needle position prior to, during, and/or after the use of the device 400. Prior to use of device 400, the needle may be in its storage position, out of the way of the channel or opening 412 where cartridge 420 is to be inserted, or out of the way of cartridge 420 once it has been inserted in base 401. In the storage position, the needle assembly may protrude laterally from the end of the base 401 and/or vertically above the base 401.

A needle assembly 445 may include a needle 430 having a first end 430a for communicating with a fluid to be injected and a second end 430c for communicating with a patient into whom the fluid is to be injected. The first end 430a and second end 430c may be oriented in the same direction (e.g. the needle may have a U shape), in opposing directions (e.g. the needle may be straight), or orthogonal to one another (e.g. the needle may include one or more curves or bends), depending on the design of the fluid delivery device 400. In some embodiments the needle ends 430a, 430c may be directed substantially orthogonal to one another to allow the fluid delivery end to communicate with a cartridge 420 and the delivery end to communicate with the patient in a low profile design. The fluid delivery device 400 may include a needle assembly 445 that includes the needle 430, which may be useful for positioning the needle 430 to be coupled with the fluid cartridge 420, the patient, or both the fluid cartridge 420 and the patient.

Figure 7A:
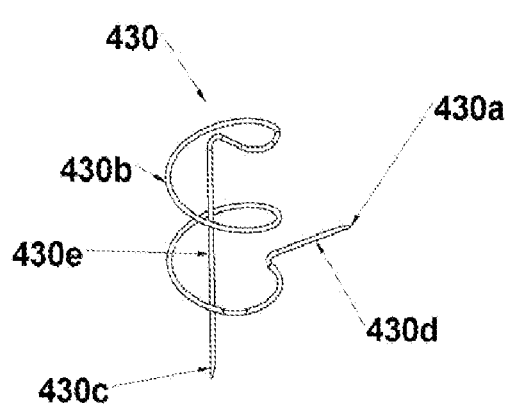
FIG. 7A is a trimetric view of a needle in accordance with an exemplary embodiment of the invention.

FIGS. 7A though 7E show exemplary details of a needle assembly 445 according to an embodiment of the invention, including a needle 430, a needle core 435, a needle assembly head 450 and a needle assembly cap 440. The needle 430 may be secured in the needle core 435 (e.g. near to the center of the needle core) and the top of the needle core 435 may be secured to underside of the needle assembly cap 440. In one embodiment, the needle assembly head 450 includes snaps 450a, defines a channel 450c, and includes ridge 450b that protrudes into channel 450c. Channel 450c may be sized and configured to receive the needle core 435. In one embodiment, channel 450c is sized and configured to not receive coiled needle center portion 430b (e.g., coiled needle center portion 430b has a greater radius or a different geometry than channel 450c). Coiled needle center portion 430b may be in contact with needle assembly head 450 and, in the storage or deployed position, be biased against needle assembly head 450.

FIG. 7A shows an exemplary needle 430 in accordance with an embodiment of the invention. The axis 430d extending between the proximal end (e.g. the fluid coupling end) 430a and needle center portion 430b may be oriented orthogonal to the axis 430e extending between the distal end (e.g. the delivery end) 430c and the needle center portion 430b. In one embodiment, the proximal end 430a penetrates the septum 416 of cartridge assembly 420 during the priming step. The distal end of the needle (e.g. the delivery end) 430c may penetrate the user's skin to deliver the fluid in the delivery step. In one embodiment, the needle center portion 430b defines a coil that flexes to allow orthogonal motion of the two ends of the needle. The needle center portion coil 430b may have a length that is configured to extend from an initial or relaxed length to an extended length as the needle assembly 445 translates from the primed position to the deployed position. The length of the coil may be configured to compress from an extended length to a more relaxed length (e.g. a shorter length or the initial length) as the needle assembly translates from the deployed position to the retracted position. In a preferred embodiment, the coil has between ½ and 3 coils, for example, about ½ coil, about 1 coil, about 1.5 coils, about 2 coils, about 2.5 coils, or about 3 coils. In some embodiments the coil has about 4 or about 5 coils. In some embodiments the coil has less than 5 coils, less than 4 coils, or less than 3 coils. In a preferred embodiment, the coil has about 2.3 or about 2.31 coils. In another embodiment, the inside diameter of the coil is large enough to fit around the outside diameter of the channel structure 450c. In a preferred embodiment, the inside diameter of the coil is large enough to fit over a compression spring that fits around the outside diameter of the channel structure 450c.

Figure 7B:
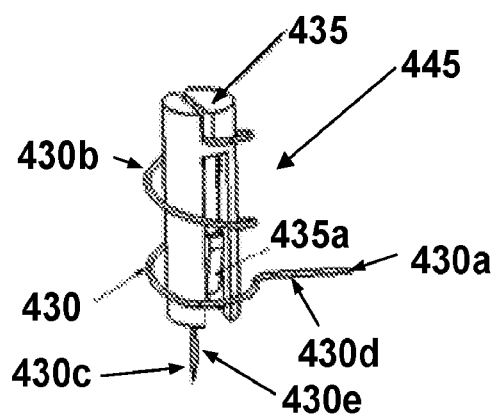
FIG. 7B is a trimetric view of the needle shown in FIG. 7A disposed over a needle core in accordance with an exemplary embodiment of the invention.

FIG. 7B shows an exemplary needle 430 mounted in the needle core 435, in accordance with an embodiment of the invention. The needle center portion 430b may coil around the exterior surface of the needle core 435. In one embodiment, the needle core 435 is sized and configured to fit within the needle center portion 430b and preferably defines a cylinder. That is, the needle center portion 430b may bend over and then coil around the needle core 435. The needle core 435 may define a lengthwise bore or slot that is sized and configured to receive the distal end 430c of the needle 430. In one embodiment, the straight distal segment extending between needle center portion 430b and distal end 430c of the needle 430 is secured within the needle core 435, exiting the core base with sufficient length protruding to achieve the desired skin penetration depth.

Figure 7C:
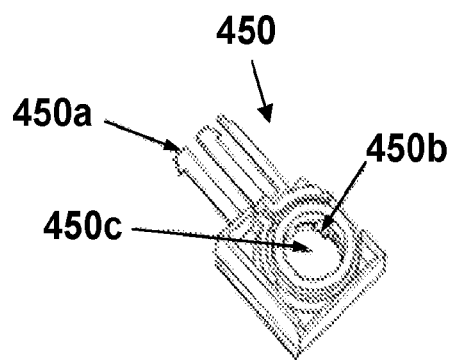
FIG. 7C is a trimetric view of a needle assembly head in accordance with an embodiment of the invention.

The needle assembly may include a lock to retain the needle in the deployed position. Such a lock is particularly advantageous in embodiments that include a coiled needle where the coiled portion of the needle is compressed in the deployed position (e.g. against needle assembly head 450, shown in FIG. 7C) and urges the needle 430 to a retracted position. Referring to FIGS. 7B and 7C, in an embodiment where the needle center portion 430b defines a coil, the needle core 435 may also include a flexing latch 435a that snaps over a counterpart feature (e.g. ridge 450b) on the inside of the needle assembly head channel 450c to reversibly lock the needle core 435 and needle 430 in the deployed position when the distal end 430c is deployed in the user's skin. In the deployed position the latch 435a may be engaged with a protrusion ridge 450b, locking the needle 430 in the deployed position with the coiled needle center portion 430b deformed (e.g. compressed). When latch 435a is released from protrusion ridge 450b the spring force of the deformed (e.g. compressed) needle center portion 430b (and/or a supplemental compression spring) may pull the needle 430 from the deployed position (and from a user's skin and/or tissue) to the retracted position and returns the coiled needle center portion 430b to a more relaxed state. In some embodiments a compression spring can also be fit around the needle core 435, e.g. inside the coiled needle center portion 430b, to aid the needle 430 spring force in withdrawing the needle from the user's tissue. In an alternative embodiment the needle assembly channel 450c may include a ridge and the needle assembly core 435 may include a complementary latch.

Figure 8:
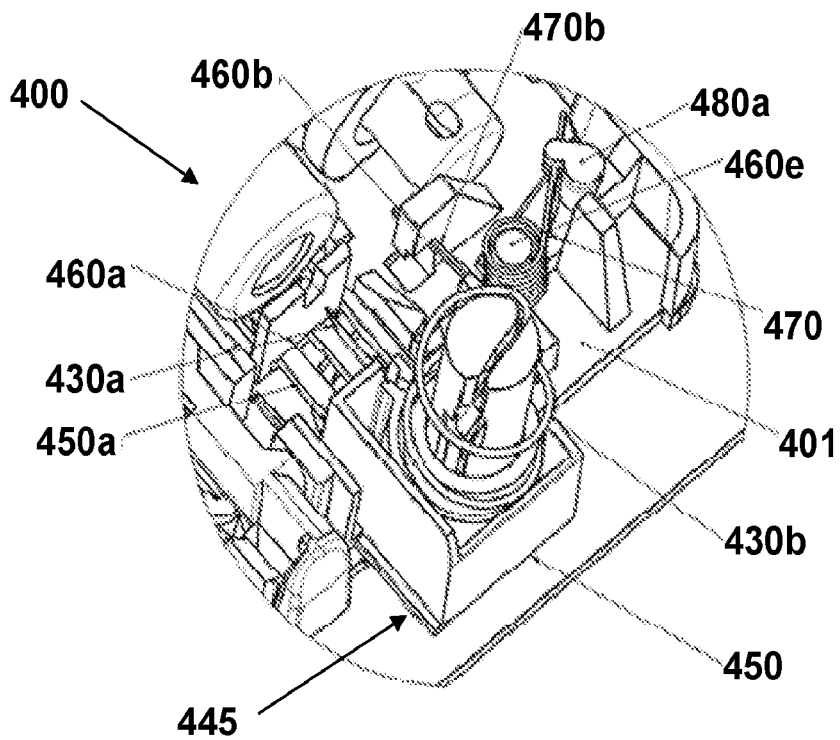
FIG. 8 is a trimetric detail view of the assembled embodiment shown in FIG. 4, in the storage position, ready for the insertion of the medicament cartridge assembly with the cover, needle assembly cap, and return spring removed for clarity.

Referring to FIG. 7C, the needle assembly head 450 may include one or more snap features 450a. Snap features 450a may be straight, as illustrated, or one or more (preferably two) of the snap features 450a may be formed with the tips flared beyond where they will be in the operation or storage of the fluid delivery device, thus reducing the need for tight tolerance in forming. In an embodiment, snap features 450a may serve as a mechanism to keep the needle assembly from translating laterally off the edge of the base 401. Referring to FIG. 8, wherein an embodiment of the needle assembly 445 is shown in the storage position (the cap 440 is not shown for visibility), the needle assembly is held in position (e.g. does not pull out of the fluid delivery device 400) by the snap features 450a on the needle assembly head 450 extending through an opening and engaging with wall 460a of the fluid delivery device base 401. The opening in wall 460a is sized and shaped to allow the arms of snap features 450a to extend through and the hooks of snap features 450a to latch onto the opening walls, preventing the needle assembly from coming out of the fluid delivery device 400. In an embodiment the opening in wall 460a is a rectangular opening perpendicular to the base 401.

Figure 7D:
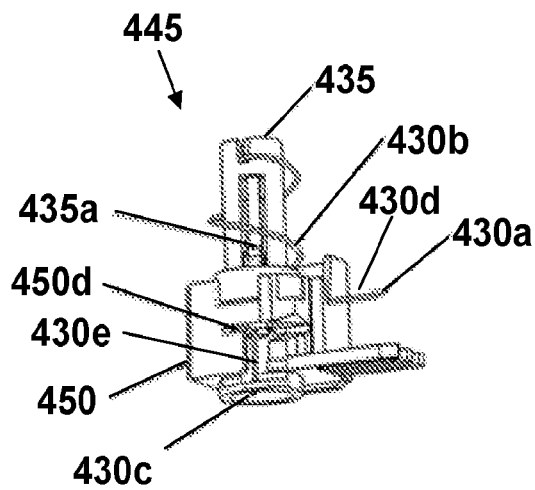
FIG. 7D is a trimetric view of a needle assembly in accordance with an embodiment of the invention, including the needle shown in FIG. 7A, the needle core shown in FIG. 7B, and the needle assembly head shown in FIG. 7C.

Referring to FIG. 7D, the needle core 435 with the needle 430 mounted in it may be disposed in channel 450c of the needle assembly head 450. In one embodiment, the radius of the coil of needle center portion 430b is large enough (e.g., the needle 430 coils around the needle core 435 loosely enough) that the needle center portion 430b falls outside of the channel 450c and rests on the needle assembly head 450. In the storage position, the coiled needle center portion 430b may be in a more relaxed state and holds the needle core 435 so that the distal tip of the needle 430c is slightly recessed within the channel 450c.

Figure 7E:
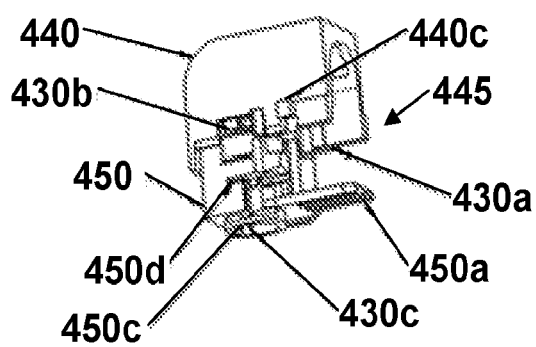
FIG. 7E is a is a trimetric view of the needle assembly of FIG. 7D, further including a needle assembly cap.

Referring to FIG. 7E, in some embodiments the needle assembly cap 440 is secured to the needle assembly core 435 so that the core 435 and the cap 440 travel together at all times.

The needle 430 in a fluid delivery device 400 can be susceptible to accidental sticks. In particular, the fluid coupling end 430a of the needle and the delivery end 430c of the needle can each be susceptible to inadvertent exposure. It may be desirable to include one or more safety mechanisms in the fluid delivery device 400 that limit inadvertent needle exposure to prevent accidental needle sticks and potential infection. Such safety mechanisms may include locks to protect the needle end from accidental exposure.

A fluid delivery device 400 may include a lock that retains the needle assembly in the storage position when a cartridge 420 is not coupled with the fluid delivery device 400. Such a lock may prevent inadvertent exposure of one or both needle ends. In an embodiment, a cartridge receiver 460d may be a flexing feature (also referred to as a receiving arm); in some embodiments the flexing feature cartridge receiver 460d functions as a lock by having a locked position in which the needle assembly 445 is retained in the initial position and an unlocked position in which the needle assembly 445 is able to translate from the initial position to the primed position. In an embodiment the cartridge receiver 460d is configured to be in the locked position when the cartridge receiver 460d is not engaged with the cartridge 420 and configured to be in the unlocked position when the cartridge receiver is engaged with the cartridge 420.

In an embodiment, the needle assembly head 450 is prevented from being pushed laterally prematurely by engaging with base 401. As shown in FIG. 9, in a storage position a cartridge receiver 460d of the base 401 may be raised vertically from the base 401 and may block the snap elements 450a from moving toward the channel or opening 412. That is, the one or more snap features 450a (e.g. a stop) may abut a cartridge receiving arm 460d on the base 401 in the storage position to prevent the needle assembly 445 from being translated into the primed position (and preventing exposure of the fluid coupling end 430a of needle 430 in the channel) prior to the cartridge 420 being inserted in the fluid delivery device 400.

Figure 10:
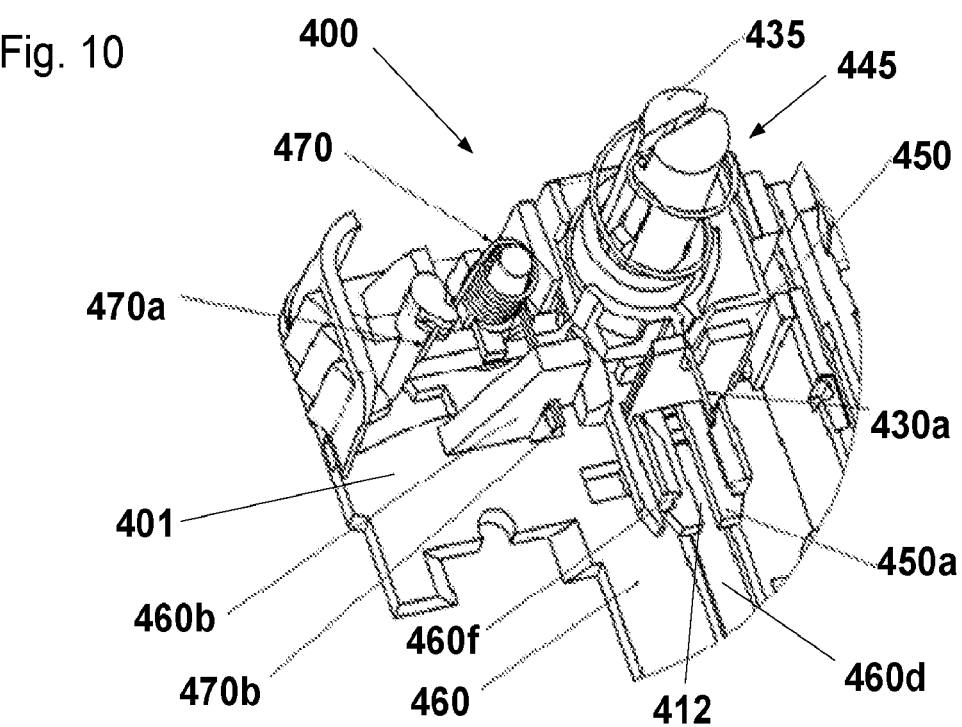
FIG. 10 is a trimetric top detail view of the assembled embodiment shown in FIG. 4 with the delivery needle engaged with the medicament cartridge and the cover, needle assembly cap, spring drive, and insertable medicament cartridge assembly removed for clarity.
Figure 11:
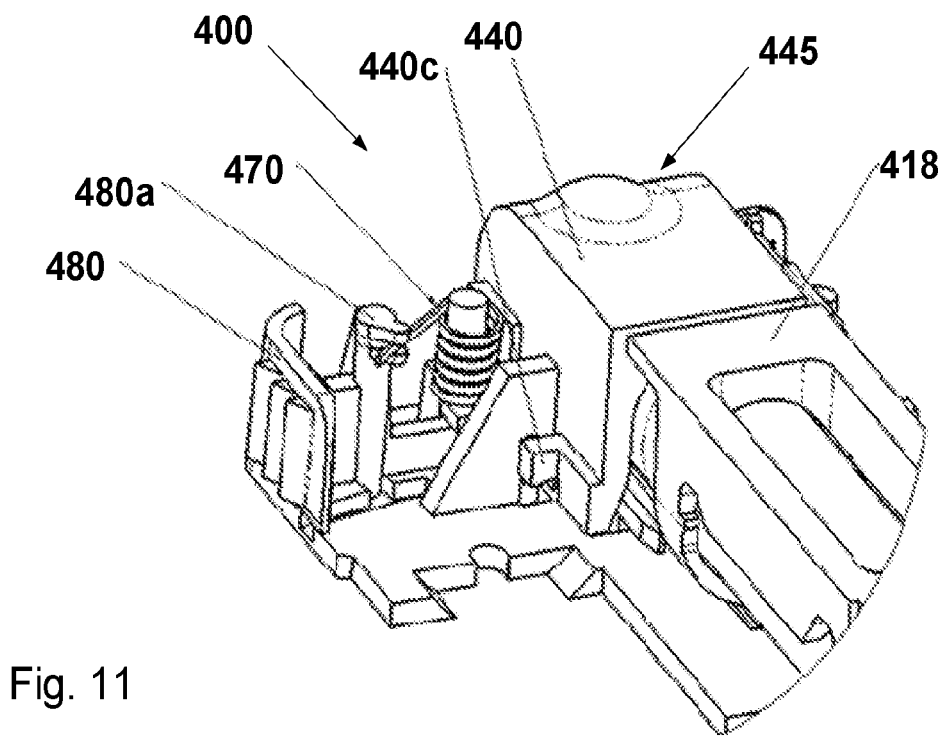
FIG. 11 is a trimetric detail view of the assembled embodiment shown in FIG. 4 with the delivery needle deployed into the patient and the cover and spring drive removed for clarity.

As described in reference to FIGS. 8-10, a cartridge receiver (e.g. flexing feature or receiving arm) 460d of the base 401 may be raised vertically from the base 401 and block the snap elements 450a from moving towards the channel 412. Placement of a cartridge 420 in the opening or channel 412 may depress the cartridge receiver (e.g. flexing feature or receiving arm) 460d out of alignment with needle assembly snap features 450a, allowing the needle assembly 445 to be pushed toward the cartridge 420 (i.e., into the primed position). For example, the cartridge receiver 460d may be configured to protrude into the channel 412 at a first angle relative to the base 401 when the cartridge 420 is not engaged with the cartridge receiver 460d and may be configured to flex to a second angle relative to the base 401 in response to engagement with the cartridge 420, wherein the first angle is greater than the second angle. The first angle, the second angle, or both the first and second angles may be acute. Depression of the cartridge receiver (e.g. flexing feature or receiving arm) 460d may disengage the cartridge receiver 460d from snap elements 450a allowing the needle assembly 445 to be moved into the primed position. In the primed position, the needle assembly 445 has been translated horizontally towards the cartridge assembly 420. The proximal end of the needle 430a may be secured to the needle assembly head 450 so that moving the needle assembly 445 from its storage position to its primed position will press the proximal end of the needle 430a through the septum 416, which seals the end of the reservoir 415.

Referring to FIG. 9, the fluid delivery device may include a finger guard 460g of the base 401. When the device 400 is in the storage position, the finger guard 460g may be disposed between the proximal tip 430a of the needle 430 and the opening or channel 412 in the base 401 for receiving cartridge 420. The finger guard 460g may prevent a user from reaching the fluid coupling end 430a of the needle by inserting a finger into the opening for the cartridge 420.

The base 401 may have a lock (e.g. a base protrusion), and the needle assembly 445 may have a complementary lock (e.g. a cap protrusion), wherein the base lock is configured to mate with the needle lock to prevent the needle assembly 445 from deploying the needle delivery end 430c when the needle fluid coupling end 430a is not coupled to a cartridge 420. In a preferred embodiment the base lock is configured to mate with the needle lock to prevent the needle assembly 445 from translating vertically when the needle assembly 445 is in the initial position and wherein the base lock is configured to be unmated from the needle lock to allow the needle assembly 445 to translate vertically when the needle assembly 445 is in the primed position. In an alternative embodiment, the base lock is configured to mate with the needle lock to prevent the needle assembly from translating laterally when the needle assembly 445 is in the initial position and wherein the base lock is configured to be unmated from the needle lock to allow the needle assembly 445 to translate laterally when the needle assembly is in the primed position.

Referring to FIG. 5, prior to the cartridge assembly 420 being inserted in a channel or opening 412 in the base 401 (i.e. in the storage position), the needle assembly 445 may be in a position that protrudes horizontally beyond the end of the base 401. In this position, the needle assembly cap 440 may be prevented from moving in the vertical direction, which thereby prevents the needle 430 from being deployed. In the storage position, motion of the cap 440 toward the base 401 may be prevented by one or more cap protrusions (e.g. 440a and 440b) on the exterior of the needle assembly 445 (e.g., on the exterior of needle assembly cap 440) and similar cap protrusion(s) on the opposite side of the needle assembly cap 440 (e.g. 440c shown in FIG. 11) engaging with or resting on top of one or more base protrusions 460c (shown in FIG. 6) protruding from the base 401 and similar features on the opposite side of the needle assembly 445. In one embodiment, in the storage position the needle assembly cap 440 is prevented from moving away from the base 401 by one or more features on the inside of the housing 403 engaging with or trapping the needle assembly cap protrusions 440a and 440b.

In one embodiment a locking mechanism includes base protrusions that, when coupled with cap protrusions of the needle assembly (e.g. in the storage position), block the needle assembly from translating vertically and exposing the needle delivery end. In a storage position, base protrusions 460c may engage with cap protrusions 440a, 440b, and 440c (440a and 440b shown in FIG. 5 and 440c shown in FIG. 7E) to prevent the needle cap assembly 440 from compressing needle center portion 430b and exposing the distal end of the needle 430c. In a primed position, cap protrusions 440a, 440b, and 440c (440a and 440b shown in FIGS. 5 and 440c shown in FIG. 7E) may be offset from base protrusions 460c (shown in FIG. 9) such that base protrusions 460c no longer block the needle cap 440 and needle assembly 445 from being depressed vertically toward base 401 to the deployed position.

The fluid delivery device 400 may further include a lock that prevents the needle assembly 445 from redeploying from the retracted position to the deployed position. Such a lock may include a bar or other barrier that blocks the needle assembly 445 from translating from the retracted position to the deployed position. In an embodiment the bar is activated when the needle assembly 445 moves from the primed position to the deployed position and is established in a blocking position when the needle assembly moves from the deployed position to the retracted position.

In one embodiment a locking mechanism includes a mechanism of preventing the needle core 435 from translating vertically after the needle 430 has been retracted from the patient's skin. In one embodiment a lockout element may extend through channel 450c after the needle core 435 and needle 430 have been retracted, thereby blocking the needle core 435 and needle 430 from being redeployed. Referring to FIG. 7D, the needle assembly head 450 may define a slot 450d, located in the side of the needle assembly head 450 and below the storage position of the needle core 435 in the channel 450c of the needle assembly head 450. In the retracted position a lockout element (e.g. torsion spring leg 470b shown in FIGS. 8-10) may extend into the slot 450d and lock the needle assembly core 435 in the retracted or storage position, for example, by impeding movement of the needle assembly core 435 through channel 450c toward base 401.

Figure 14:
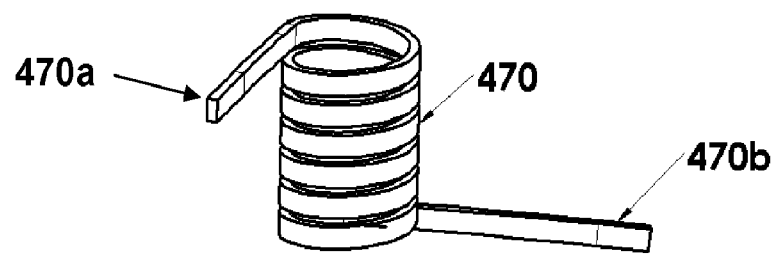
FIG. 14 is a torsion spring in accordance with an embodiment of the invention.

In one embodiment, the lockout element may be a leg of a torsion spring. Referring to FIG. 9, a torsion spring 470 may be mounted over a base boss 460e with its legs 470a, 470b deflected to tighten the spring coils. The torsion spring 470 may be biased against (e.g. one leg 470a presses against) a feature 480a of the needle release button 480, holding the release button 480 in place. The other torsion spring leg 470b of the torsion spring may be restrained from contacting the needle assembly by a hook 460b of the base 401. The bottom of the base boss 460e may be located to position the bottom of the torsion spring at the same height as the slot 450d in the needle assembly head 450. As shown in FIG. 14, in some embodiments the torsion spring has a rectangular cross section. In other embodiments the torsion spring has a circular cross section.

In an embodiment a fluid delivery device 400 may include multiple safety mechanisms that prevent accidental needle exposure at different stages of fluid delivery.

FIGS. 9 and 10 show the elements of the fluid delivery device 400 according to one embodiment, after a cartridge assembly 420 has been inserted in the fluid delivery device 400 (though the cartridge assembly itself is not shown to allow the relationship between the other elements to be seen). The unconnected end of the cartridge receiver 460d of the base 401 may be moved down by the cartridge 420 so that it lies below the level of the snap features 450a on the needle assembly head 450. The user can now press on the end of the needle assembly 445 to move the assembly to the primed position (shown in FIG. 10) and cause the snap features 450a on the needle assembly head 450 to engage base features 460f, locking the needle assembly 445 in the primed position (e.g., proximal end 430a of the needle 430 in contact with fluid reservoir 415, but the distal end 430c not deployed into the user's skin). Moving the needle assembly 445 to the primed position may move the needle assembly cap 440 such that the cap protrusions 440a and 440b (shown in FIG. 5) and 440c (shown in FIG. 7E) are no longer over and restrained by base protrusions 460c, and the needle assembly core 435 and distal end of the needle 430c can be moved vertically down so that the distal end of the needle 430c extends into the user's tissue.

The user may now press down on the top of the needle assembly cap 440 (shown in FIG. 11) to move the needle assembly cap 440, the attached needle assembly core 435 (shown in FIG. 10 with the needle assembly cap removed for clarity), and the needle 430 (shown in FIG. 10 with the needle assembly cap removed for clarity) down so that the distal end 430c of the needle 430 penetrates the user's skin (i.e., the deployed position).

In the primed position, needle core 435 may be depressed vertically through channel 450c toward base 401, the needle center portion 430b may be compressed, and the distal end 430c may extend beyond the base of channel 450c. Thus, the distal end of the needle 430c can be pushed into tissue by pushing down on the cap 440 from the primed position.

When the needle assembly cap 440 is depressed (i.e. deployed), the flexing latch feature 435a may snap over ridge 450b (as shown in FIGS. 7B and 7C) on the inside of the needle assembly head channel 450c and hold the needle core 435 and needle 430 in the depressed position, making the fluid connection between the fluid (e.g. medicament) reservoir 415 and the patient's subcutaneous (or other) tissue. In the depressed state (i.e., the deployed state), a cap protrusion 440c on the side of the needle assembly cap 440 may dislodge the torsion spring leg 470b of the torsion spring 470 from the hook 460b of the base 401. The spring force of the torsion spring 470 may carry the torsion spring leg 470b against the side of the needle assembly cap 440, where it rests when the needle assembly 445 is in the deployed position.

Figure 12:
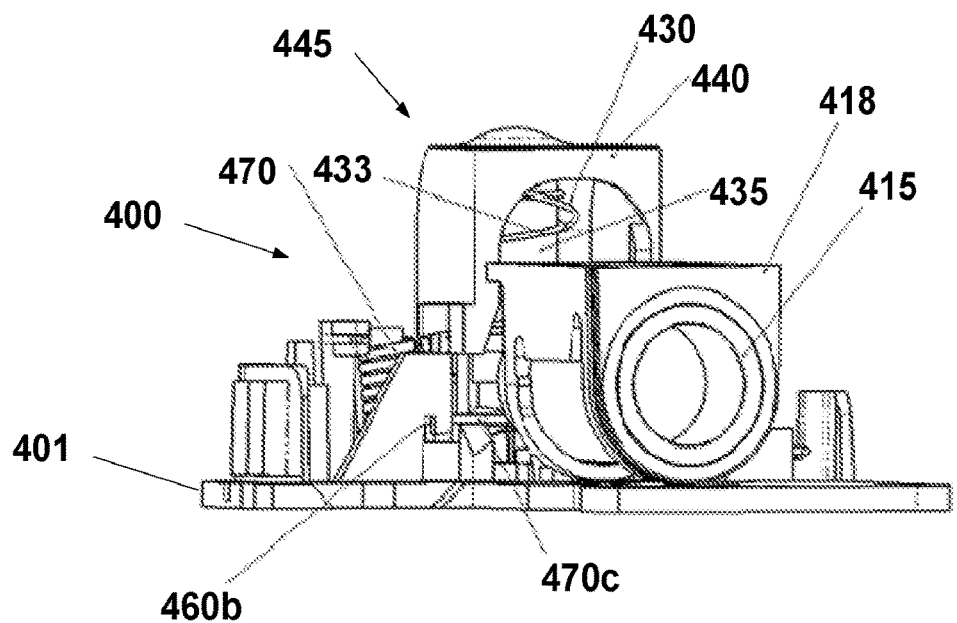
FIG. 12 is a near end view of the assembled embodiment shown in FIG. 4 with the delivery needle retracted from the patient and the cover, hydraulic drive system, piston, and spring drive removed for clarity.
Figure 13:
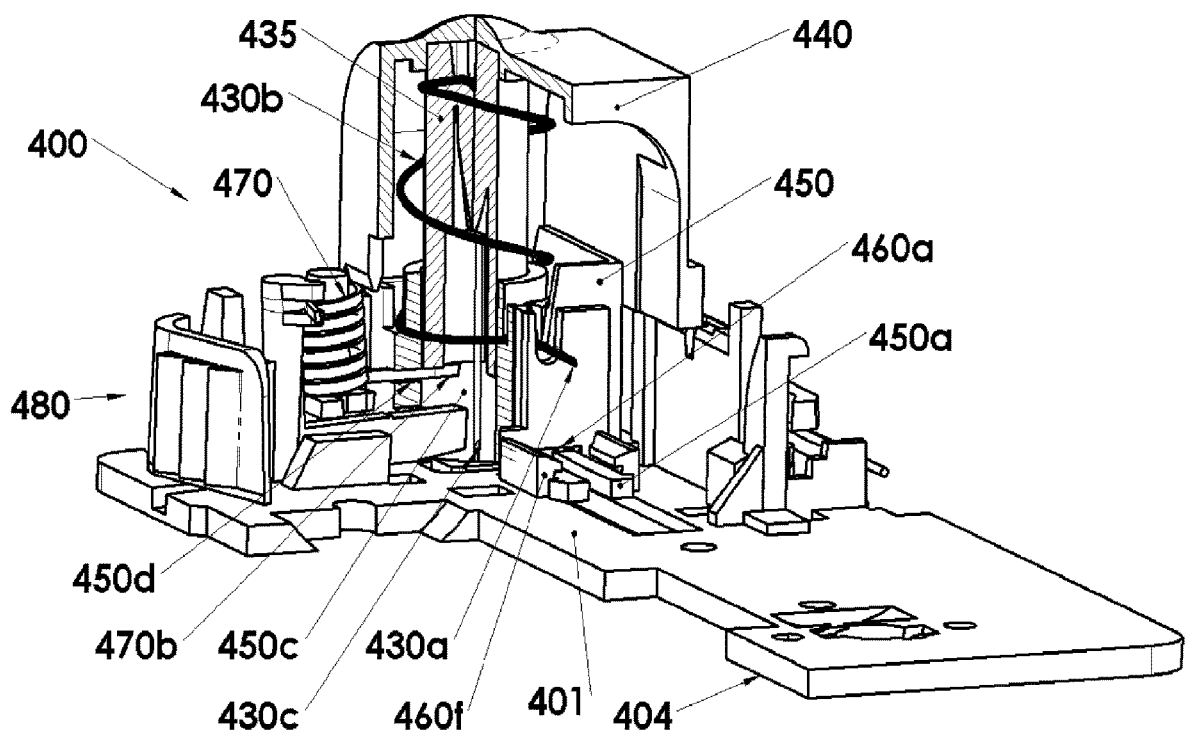
FIG. 13 is a trimetric side cut-away view of the assembled embodiment shown in FIG. 4 with the delivery needle retracted from the patient, and the cover, hydraulic drive system, piston, and spring drive removed for clarity.

When the user is done with the fluid delivery device 400 he or she may press the needle release button 480. The opposite end of the needle release button 480c (shown in FIG. 9) may push the flexing latch 435a off of the ridge 450b on the inside of the needle assembly head channel 450c. This may release the needle core 435 so that the needle core 435, needle 430 and cap 440 can return to the primed position under the force of the coil of needle 430 and/or a supplemental compression spring (shown nested within the coil of the needle center portion 430b of the needle 430). In an embodiment, as the needle assembly cap 440 moves up vertically away from base 401, the torsion spring leg 470b is blocked from being carried vertically upward with the needle assembly cap 440 by feature 460*b*. The torsion spring leg 470*b* of the torsion spring 470 may continue to press against the needle assembly cap 440 as needle assembly cap 440 moves vertically upward until slot 450*d* is exposed, at which point the force of tension spring 470 may push torsion spring leg 470*b* through slot 450*d* up against the needle core 435. Once the needle core 435 has retracted so that the bottom is above the slot 450*d*, the torsion spring leg 470*b* can extend into channel 450*c*. In this final position, the torsion spring leg 470*b* may block the channel 450*c* in the needle assembly head 450 preventing the needle core 435 from being depressed into channel 450*c* and preventing needle 430 from being redeployed, as shown in FIGS. 12 and 13.

The torsion spring 470 may be designed such that the spring applies an appropriate amount of return force on the needle release button 480. In some embodiments it does not apply so much force on the side of the needle assembly cap 440 that it interferes with the cap 440 moving freely (and thus interfering with the needle 430 returning to the primed position at the end of use). A torsion spring 470's force may be a function of the wire size (e.g. cross-section or gauge), the number of coils, and the coil diameter. There may be a limitation on the diameter of the coils and the number of coils that will fit in the available space in a small fluid delivery system. Another available variable for reducing the spring force is the torsion spring 470 wire size. Typically, to reduce the spring constant, the wire diameter is reduced, but reducing the may result in the torsion spring leg 470*b* of the spring not being strong enough to effectively block the channel 450*c* once the needle 430 is withdrawn (e.g., in the retracted position). In one embodiment, the torsion spring 470 is made of a wire having a non-circular cross section such as oval or a rectangular cross section wire as shown in FIG. 14. A non-circular cross section may allow the spring constant to be reduced by shrinking the thickness of the wire perpendicular to the coil axis. The ability to block the channel 450*c* can be increased by increasing the height of the wire parallel to the axis of the coil. Increasing the height of the wire has a much smaller impact on the spring constant than increasing the width, so by using, for example, a rectangular cross section, the spring force can be reduced to an acceptable level while the channel 450*c* blocking ability of the torsion spring leg 470*b* is maintained or increased. In an embodiment the torsion spring 470 has a cross section with a first axis larger than a second axis, wherein the second axis is oriented orthogonal to the first axis.

In the fluid delivery device as shown in FIG. 8, the torsion spring may be deformed such that one torsion spring leg 470*b* of the torsion spring 470 is captured by feature 460*b* (e.g. a hook) of the base 401. This hook may be positioned at a specific height so that the torsion spring leg 470*b* is not released until the cap 460 and needle core 435 combination have moved vertically away from the base 401 in channel 450*c* to prevent redeployment of needle 430, (e.g. until the needle assembly is ready to be locked down). This height may potentially be different from the height of the bottom of the torsion spring coil 470 so the end of the torsion spring leg 470*b* may be deflected along the axis of the torsion spring. This can require more force than is desirable for storage, especially if the torsion spring has a rectangular wire profile. In one embodiment, the post that the torsion spring is mounted on 460*e* is sized and tapered to allow the torsion spring to cant. With the coil canted, much of the displacement required in the torsion spring 470 to position the torsion spring leg 470*b* in the hook 460*b* may be created by deformation in the torsion coils and not the bending of the torsion spring leg 470*b* alone. This canting in the storage position may not result in canting in the final lock out configuration, as the slot 450*d* in the needle assembly head 450 may be positioned at a height similar to the base of the coil and thus the spring may not be canted in its final position (shown in FIG. 12).

It may be desirable to provide a medicament maintained separately from a carrier fluid or diluent (or solvent) and mix the medicament and diluent immediately prior to administration to the patient (e.g. when the cartridge 420 is placed in the fluid delivery device 400). It may alternatively be desirable to provide two different medicaments, maintained separately in storage, and mixed immediately prior to administration (e.g. when the cartridge 420 is placed in the fluid delivery device 400). In an embodiment a cartridge 420 provides two material chambers, which are maintained separate during storage but can be fluidly connected immediately prior to administration. In an embodiment the fluid chambers may be separated by a moveable barrier and fluidly connected when the barrier is moved to be aligned with a bypass 424*a*.

Figure 15:
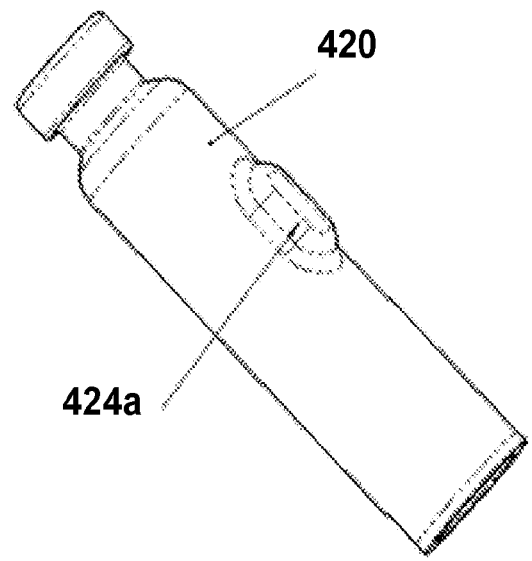
FIG. 15 is a trimetric view of an insertable medicament cartridge in accordance with an embodiment of the invention.

Referring to FIG. 15, in an embodiment, the fluid cartridge 420 is a dual chamber cartridge with a piston bypass 424*a*. The piston bypass 424*a* may provide a connection between a first reservoir 421 and a second reservoir 429 in the fluid cartridge 420 allowing fluid from one reservoir to flow around a barrier separating the first reservoir 421 and second reservoir 429 and for the material in the first reservoir and the second reservoir to mix. Accordingly, in an embodiment the piston bypass 424*a* is a trench extending axially from the first reservoir 421 to the second reservoir 429, The piston bypass 424*a* may have a width narrower than the barrier, such that the barrier is retained in the body of the fluid cartridge and does not catch on or fall into the bypass 424*a* as it moves into alignment with the bypass 424*a*. As shown in FIG. 16B, the cartridge 420 may have a first material (e.g. fluid or medicament) stored in a first reservoir 421 and a second material (e.g. fluid or medicament), stored in a second reservoir 429. The first fluid and the second fluid may be mixed just prior to delivery. Typically one of the first and second materials is a dry lyophilized material and the other of the first and second materials is a diluent. It may be desirable to maintain a first material and a second material separate until immediately before administration of the two materials to a patient. It may be desirable to mix the first material and the second material immediately before administration. A fluid delivery device that allows a patient to mix the first material and second material as part of the act of injection may increase ease of use, and compliance. Moreover, a fluid delivery system and cartridge that include premeasured amounts of the first material and the second material in closed system may increase accuracy of administration by limiting the opportunities for loss of material during mixing.

A fluid delivery device 400 may include a base 401, and a cartridge 420 configured to be inserted into the fluid delivery device base 401, the cartridge 420 comprising: a septum 416 having a pierceable portion; a first slidable piston 424; a first reservoir 421 between the first slidable piston 424 and the septum 416; a second slidable piston 425; a second reservoir 429 formed between the first slidable piston 424 and the second slidable piston 425; and a piston bypass 424*a* fluidly coupling the first reservoir 421 and the second reservoir 429 when the first slidable piston 424 is positioned in axial alignment with the piston bypass 424*a*. In an embodiment a fluid delivery device 400 further includes a hydraulic drive including hydraulic drive fluid that is configured to push the second slidable piston 425 toward the first slidable piston 424. The hydraulic drive may include a bolus piston 406 that is configured to push the hydraulic fluid toward the second slidable piston 425. The hydraulic drive may further include a stem 411*a* that is in physical contact with the bolus piston 406 and is configured to push the bolus piston 406 toward the hydraulic fluid. In an embodiment the stem 411*a* may be a bolus pawl and include a ratchet system. The hydraulic drive may include a button configured to actuate movement of the hydraulic drive fluid. The movement may be stepwise or continuous. In another embodiment a fluid delivery device 400 further includes a stem that is configured to push the second slidable piston 425 toward the first slidable piston 424. The fluid delivery device 400 may include a button that is in physical contact with the stem and is configured to push the stem and second slideable piston 425 toward the first slidable piston 424. The hydraulic drive may include a button configured to actuate movement of the stem. The movement may be stepwise or continuous.

A method of mixing a first material and a second material in a fluid delivery device 400 that includes a hydraulic drive fluid may include inserting a cartridge 420 in the fluid delivery device 400, the cartridge 420 having a septum 416, a first slidable piston 424, a first reservoir 421 containing a first material and positioned between the first slidable piston and the septum, a second slidable piston 425, a second reservoir 429 containing a second material and formed between the first slidable piston 424 and the second slidable piston 425, and a piston bypass 424*a*; and displacing the hydraulic drive fluid, wherein the hydraulic fluid is in mechanical communication with the second slidable piston 425, to displace the second slidable piston 425 towards the first slidable piston 424. The second material may be urged through the piston bypass 424*a* into the first reservoir 421 as the second slidable piston 425 is brought into contact with the first slidable piston 424. Alternatively, a method of mixing a first material and a second material in a fluid delivery device 400 that includes a stem may include inserting a cartridge 420 in the fluid delivery device 400, the cartridge 420 having a septum 416, a first slidable piston 424, a first reservoir 421 between the first slidable piston 424 and the septum 416 containing a first material, a second slidable piston 425, a second reservoir 429 formed between the first slidable piston 424 and the second slidable piston 425 containing a second material, and a piston bypass 424*a*; and displacing the stem, wherein the stem is in mechanical communication with the second slidable piston 425, to displace the second slidable piston 425 towards the first slidable piston 424. The second material may be urged through the piston bypass 424*a* into the first reservoir 421 as the second slidable piston 425 is brought towards and/or into contact with the first slidable piston 424.

In some embodiments the displacing may be actuated by pressing a button in physical communication with the hydraulic drive or the stem. In some embodiments the displacing may be stepwise. In some embodiments the displacing may be continuous.

Figure 16A:
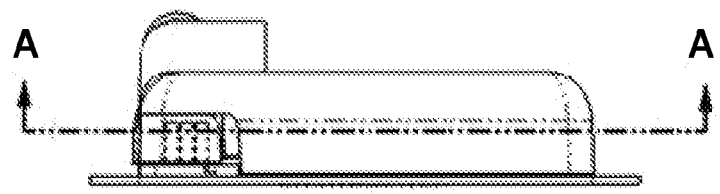
FIG. 16A is a side view of the fluid delivery device in accordance with an embodiment of the invention.
Figure 16B:
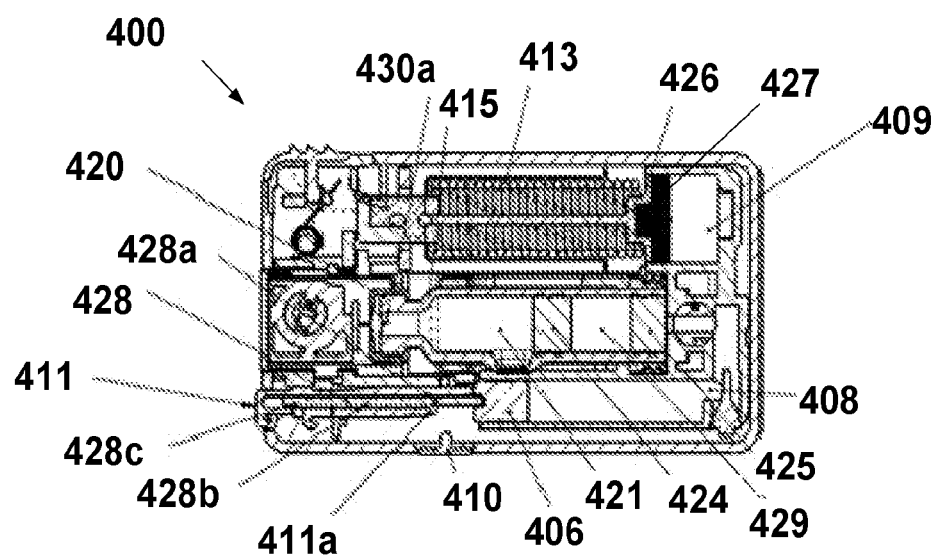
FIG. 16B is a top cut-away view of the fluid delivery device shown in FIG. 16A, taken along a plane indicated by line A-A, with the second piston in a first position.

FIGS. 16B through 18 show section views of an exemplary fluid delivery device 400 depicted in FIG. 16A. Referring to FIG. 16B, the cartridge 420 may be arranged with a first piston (e.g. a barrier piston) 424, and a first reservoir 421 containing a first material (for example, dry or liquid medicament), a second piston (e.g. a proximal piston) 425, a second reservoir 429 containing a second material (for example, a liquid diluent).

The first piston 424 may initially be positioned proximal to the bypass 424*a* so that the contents of reservoirs 421 and 429 are isolated for storage. In use, the device may first be primed so that the needle fluid coupling end 430*a* penetrates the septum of the cartridge 416 but the needle delivery end 430*c* is not yet deployed into a patient. This may result in a fluid path between the first reservoir 421 and the exterior environment (through needle 430) allowing air or storage gas in first reservoir 421 to escape during drug reconstitution. While holding the device with the septum end highest, the device bolus button 411 may be activated by the user pressing the bolus release button 410. The bolus release button 410 may release bolus button 411, positioning bolus button 411 such that a user can push the bolus button 411 to drive bolus piston 406. In one embodiment, the bolus release button 410 and the bolus button 411 function in the same manner as the bolus system described in U.S. Patent Application Publication No. 2013/0046239, incorporated herein by reference in its entirety.

In an embodiment the bolus button 411 drives the bolus piston 406, which in turn drives hydraulic fluid through the chamber 408 to the proximal side of the second piston 425. In an embodiment the bolus button 411 drives a bolus button stem 411*a*, which in turn drives the bolus piston 406, which in turn drives hydraulic fluid through the chamber 408 to the proximal side of the second piston 425. The hydraulic fluid may urge the second piston 425 forward and, because the space (e.g. the second reservoir) 429 between the second piston 425 and first piston 424 is filled with liquid, the first piston 424 moves as well. Bolus button 411 may form part of a bolus ratchet system, including a bolus button 411, and a bolus button stem 411*a*. In an embodiment bolus button stem 411*a* is a bolus button pawl and includes a series of ratchet mechanism catches 428*a*, 428*b* and 428*c*. A bolus ratchet system may allow a user to push bolus button 411 forward, mixing and/or delivering the first and second material to the patient, and prevents the user from retracting the bolus button 411 and drawing fluid into needle 430 from the patient. In one embodiment, full dilution requires multiple presses of the bolus release button 410 and the bolus button 411 moving the bolus button stem 411*a* into a series of ratchet mechanism catches 428*a*, 428*b* and 428*c*.

Figure 17:
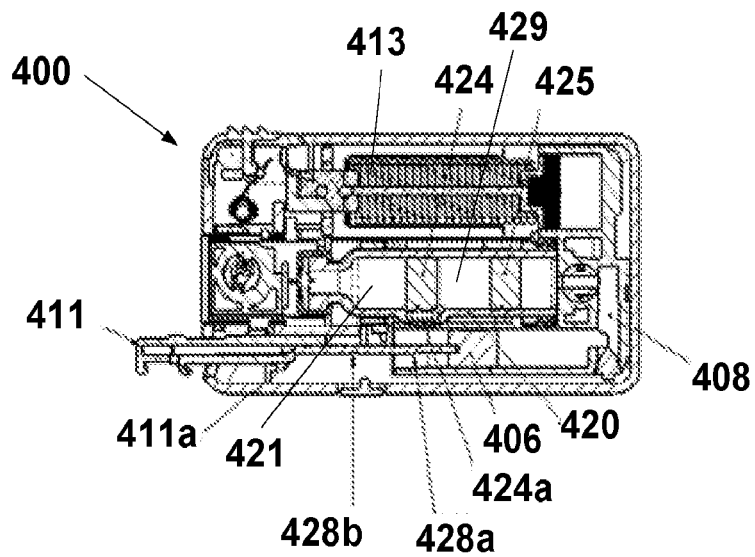
FIG. 17 is a top cut-away view of the fluid delivery device shown in FIG. 16A, taken along a plane indicated by line A-A, with the second piston in a second position.

Referring to FIG. 17, in an embodiment the user continues to push the bolus button 411 ratchet system (shown in its released and extended position) and after a set amount of piston motion, the first piston 424 will reach a position where it is within the extent of the piston bypass 424*a*. When the first piston 424 is approximately aligned with piston bypass 424*a*, the second material (e.g. diluent) fluid can flow around the first piston 424 into the first reservoir (e.g. medicament chamber) 421. The piston bypass 424*a* may be sized and configured so that the resistance to the flow around the first piston 424 is less than the force to move the first piston 424. As the user pushes the bolus button 411, the second piston 425 will continue to move toward the first piston 424, emptying the second reservoir (e.g. diluent chamber) 429.

Figure 18:
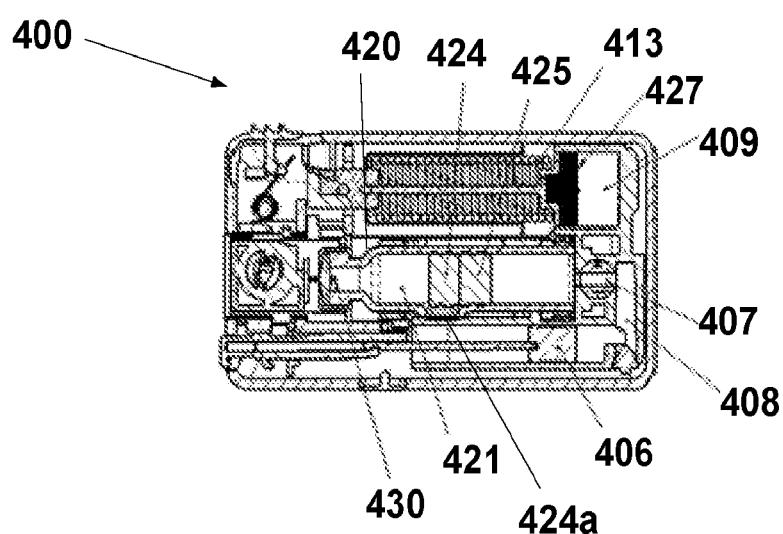
FIG. 18 is a top cut-away view of the fluid delivery device shown in FIG. 16A, taken along a plane indicated by line A-A, with the second piston in a third position.

Referring to FIG. 18, in an embodiment, once the second piston 425 has come into contact with the first piston 424, all or essentially all of the second material (e.g. diluent) has been delivered to the first reservoir (e.g. medicament chamber) 421. In one embodiment, this is the limit of the bolus mechanism so the bolus button 411 cannot be pushed farther. In one embodiment the user now waits a specified time for the first and second materials (e.g. drug and diluent) to mix. This time could be spent, for example, applying the fluid delivery device 400 to the skin. After the specified time, the basal delivery system is started by releasing one or more springs 413 which apply force to the hydraulic fluid in chamber 409 through piston 427 and the hydraulic fluid starts to flow from chamber 409 through a metering channel (not shown) to chamber 408 and on into the proximal end of the cartridge 420 urging the pair of pistons 424 and 425 forward expelling the medicament at the designed rate. In a preferred embodiment, the spring is released by withdrawing a retaining pin. In another embodiment, the spring is released by the removal of one or more retaining catches. In another embodiment, the spring is released by the rotation of an element releasing a catch retaining the spring.

In one embodiment, full dilution requires a single press of the bolus release button 410 and the bolus button 411 moving the bolus piston the full length of its travel. In another embodiment full dilution requires two or more presses of the bolus release button 410, with the bolus button 411 urging the second piston 425 a portion of the distance between the initial position of the second piston 425 and the first piston 424.

In one embodiment, the needle 430 is mounted on the cartridge 420 before insertion and the insertion of the cartridge moves the pistons to their fully reconstituted position.

In one embodiment, the dual chamber cartridge 420 is inserted into the fluid delivery device 400 in the factory and there is no need for a hydraulic oil valve 407 to hold the hydraulic fluid in place as the second piston 425 keeps the hydraulic fluid in place until the bolus button is pressed initiating the reconstitution process.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A fluid delivery device comprising:
    a housing having a base including a bottom surface and a cartridge receiver configured to receive a cartridge, the cartridge having a fluid reservoir and a septum configured to be generally perpendicular to the bottom surface when the cartridge is engaged with the cartridge receiver;
    a needle assembly having a needle, the needle having a delivery end, a fluid coupling end, and a central portion located between the delivery end and the fluid coupling end, the fluid coupling end being fluidly disengaged from the fluid reservoir in an initial position, the fluid coupling end being fluidly coupled with the fluid reservoir in a primed position, the needle assembly being configured to translate laterally relative to the base from the initial position to the primed position, the needle assembly having one or more snap features; and
    a channel for receiving the cartridge,
    wherein the cartridge receiver has a locked position in which the needle assembly is retained in the initial position and an unlocked position in which the needle assembly is able to translate from the initial position to the primed position,
    wherein the cartridge receiver is configured to be in the locked position when the cartridge receiver is not engaged with the cartridge and configured to be in the unlocked position when the cartridge receiver is engaged with the cartridge,
    wherein the cartridge receiver, when in the locked position, is configured to be raised vertically from the base and block the one or more snap features from moving towards the channel, and
    wherein the cartridge receiver is configured to be depressed out of alignment with the one or more snap features on placement of a cartridge in the channel, allowing the needle assembly to be pushed toward the cartridge.

2. The fluid delivery device of claim 1, wherein the needle assembly has a stop, the cartridge receiver abutting the stop in the locked position to retain the needle assembly in the initial position.

3. The fluid delivery device of claim 1, wherein the cartridge receiver is configured to protrude into the channel at a first angle relative to the base when the cartridge is not engaged with the cartridge receiver.

4. The fluid delivery device of claim 3, wherein the cartridge receiver is configured to flex to a second angle relative to the base in response to engagement with the cartridge, wherein the first angle is greater than the second angle.

5. The fluid delivery device of claim 1, wherein the needle assembly is configured to translate vertically relative to the base to a deployed position.

6. The fluid delivery device of claim 5, wherein the needle assembly is configured to be moveable to the deployed position only after being moved to the primed position, wherein the delivery end of the needle extends past the bottom surface of the base in the deployed position.

7. The fluid delivery device of claim 1, wherein an axis extending between the delivery end of the needle and the central portion of the needle is generally orthogonal to an axis extending between the fluid coupling end of the needle and the central portion of the needle.

8. The fluid delivery device of claim 1, wherein the central portion of the needle defines a coil.

9. The fluid delivery device of claim 5, wherein the central portion of the needle has a length that is configured to be deformed as the needle assembly translates from the primed position to the deployed position.

10. The fluid delivery device of claim 1 further comprising:
an actuator and a hydraulic chamber,
wherein the actuator is configured to deliver a force to the cartridge through a fluid contained in the hydraulic chamber.

11. The fluid delivery device of claim 1, the needle assembly further comprising:
a needle assembly core and a needle assembly head, the delivery end of the needle extending along an axial direction through the needle assembly core and the needle assembly head defining a channel sized and configured to receive the needle assembly core, the needle assembly core having one of a latch and a protrusion, the needle assembly head having the other of a latch and a protrusion,
wherein the latch is configured to releasably engage with the protrusion to lock the needle assembly in a deployed position.

12. The fluid delivery device of claim 11 further comprising:
a needle release assembly having a needle release button configured to disengage the latch from the protrusion when actuated.

13. The fluid delivery device of claim 12, wherein the central portion of the needle is configured to retract the needle assembly from the deployed position to a retracted position when the needle release button is actuated, wherein the delivery end of the needle does not extend past the bottom surface of the base in the retracted position.

14. The fluid delivery device of claim 13, wherein the base further has a retention hook and the needle release assembly further has a torsion spring biased against the needle release button, the torsion spring having a first leg and a second leg, the first leg engaged with the needle release button and the second leg configured to releasably engage with the retention hook in the initial, primed, and deployed positions, and configured to extend into the needle assembly head channel, substantially perpendicular to the axis of the channel, in the retracted position.

15. The fluid delivery device of claim 14, wherein the torsion spring has a rectangular cross-section.

16. An assembly comprising the fluid delivery device according to claim 10 in combination with a cartridge configured to be inserted into the fluid delivery device, the cartridge having a septum having a pierceable portion, a first slidable piston, a first reservoir between the first slidable piston and the septum, a second slidable piston, a second reservoir formed between the first slidable piston and the second slidable piston, and a piston bypass fluidly coupling the first reservoir and the second reservoir when the first slidable piston is positioned in axial alignment with the piston bypass,
wherein the second slidable piston is configured to be pushed into physical contact with the first slidable piston by the actuator.

17. The assembly of claim 16, wherein the first reservoir is prefilled with a first material and the second reservoir is prefilled with a second material.

18. The assembly of claim 17, wherein one of the first and second materials is a diluent and the other of the first and second materials is a medicament.

19. A method of mixing a first material and a second material in the assembly according to claim 16, the fluid delivery device including hydraulic drive fluid, the method comprising:
inserting the cartridge into the fluid delivery device, the first reservoir of the cartridge containing a first material, and the second reservoir of the cartridge containing a second material; and
displacing the hydraulic drive fluid, wherein the hydraulic drive fluid is in mechanical communication with the second slidable piston, to displace the second slidable piston towards the first slidable piston,
wherein the second material is urged through the piston bypass into the first reservoir as the second slidable piston is brought into contact with the first slidable piston.

\* \* \* \* \*